(12) United States Patent
Finley et al.

(10) Patent No.: US 9,066,701 B1
(45) Date of Patent: Jun. 30, 2015

(54) SYSTEMS AND METHODS FOR PERFORMING NEUROPHYSIOLOGIC MONITORING DURING SPINE SURGERY

(71) Applicant: NuVasive, Inc., San Diego, CA (US)

(72) Inventors: Eric Finley, Poway, CA (US); James Gharib, San Diego, CA (US); Richard A. O'Brien, Westminster, MD (US); Robert Snow, Phoenix, MD (US)

(73) Assignee: NuVasive, Inc., San Diego, CA (US)

( * ) Notice: Subject to any disclaimer, the term of this patent is extended or adjusted under 35 U.S.C. 154(b) by 228 days.

(21) Appl. No.: 13/761,098

(22) Filed: Feb. 6, 2013

Related U.S. Application Data

(60) Provisional application No. 61/595,627, filed on Feb. 6, 2012.

(51) Int. Cl.
*A61B 1/32* (2006.01)

(52) U.S. Cl.
CPC ........................................ *A61B 1/32* (2013.01)

(58) Field of Classification Search
USPC ....................... 600/201–246; 606/90, 99, 129
See application file for complete search history.

(56) References Cited

U.S. PATENT DOCUMENTS

| | | |
|---|---|---|
| 1,194,319 A | 8/1916 | Pretts |
| 2,693,795 A | 11/1954 | Grieshaber |
| 2,736,002 A | 2/1956 | Oriel |
| 2,807,259 A | 9/1957 | Guerriero |
| 3,467,079 A | 9/1969 | James |
| 3,509,873 A | 5/1970 | Karlin |
| 3,680,546 A | 8/1972 | Asrican |
| 3,724,449 A | 4/1973 | Gauthier |
| 3,740,839 A | 6/1973 | Otte |
| 3,785,368 A | 1/1974 | McCarthy et al. |
| 3,888,117 A | 6/1975 | Lewis |
| 3,998,217 A | 12/1976 | Trumbull |
| 4,010,741 A | 3/1977 | Gauthier |
| 4,156,424 A | 5/1979 | Burgin |
| 4,165,746 A | 8/1979 | Burgin |
| 4,545,374 A | 10/1985 | Jacobson |
| 4,617,916 A | 10/1986 | LeVahn |

(Continued)

FOREIGN PATENT DOCUMENTS

| | | |
|---|---|---|
| CA | 1142826 | 3/1983 |
| CN | 203506775 | 4/2014 |

(Continued)

OTHER PUBLICATIONS

"Electromyography System," International Search Report from International Application No. PCT/US00/32329, Apr. 27, 2001, 9 pages.

(Continued)

*Primary Examiner* — Andrew Yang
*Assistant Examiner* — Olivia C Chang
(74) *Attorney, Agent, or Firm* — Jonathan Spangler; Heather Prado

(57) ABSTRACT

A surgical access system comprising a tissue retraction assembly equipped with two or more electrodes for use in monitoring the status of nearby neural structures, including the localized depth of neural structures relative to one or more components of the tissue retraction assembly. Additional neurological testing may be performed to monitor the health and status of the neural structures during the portions of the surgical procedure in which the tissue retraction assembly is used to maintain the operative corridor.

9 Claims, 22 Drawing Sheets

(56) References Cited

U.S. PATENT DOCUMENTS

| | | |
|---|---|---|
| 4,627,421 A | 12/1986 | Symbas |
| 4,726,356 A | 2/1988 | Santilli |
| 4,813,401 A | 3/1989 | Grieshaber |
| 4,945,896 A | 8/1990 | Gade |
| 4,955,884 A | 9/1990 | Grossi |
| 4,962,766 A | 10/1990 | Herzon |
| 5,052,374 A | 10/1991 | Alvarez-Jacinto |
| 5,152,279 A | 10/1992 | Wilk |
| 5,195,505 A | 3/1993 | Josefsen |
| 5,199,419 A | 4/1993 | Remiszewski |
| 5,231,974 A | 8/1993 | Giglio |
| 5,280,782 A | 1/1994 | Wilk |
| 5,284,153 A | 2/1994 | Raymond et al. |
| 5,284,154 A | 2/1994 | Raymond et al. |
| 5,339,801 A | 8/1994 | Poloyko |
| 5,375,481 A | 12/1994 | Cabrera |
| 5,474,056 A | 12/1995 | Laborie |
| 5,474,558 A | 12/1995 | Neubardt |
| 5,520,610 A | 5/1996 | Giglio |
| 5,601,608 A | 2/1997 | Mouchawar |
| 5,772,583 A | 6/1998 | Wright |
| 5,775,331 A | 7/1998 | Raymond et al. |
| 5,779,642 A | 7/1998 | Nightengale |
| 5,785,647 A | 7/1998 | Tompkins |
| 5,806,522 A | 9/1998 | Katims |
| 5,807,270 A | 9/1998 | Williams |
| 5,830,150 A | 11/1998 | Palmer et al. |
| 5,830,151 A | 11/1998 | Hadzic et al. |
| 5,885,210 A | 3/1999 | Cox |
| 5,902,233 A | 5/1999 | Farley |
| 5,928,158 A | 7/1999 | Aristides |
| 5,935,131 A | 8/1999 | Bonutti |
| 5,944,658 A | 8/1999 | Koros |
| 5,947,896 A | 9/1999 | Sherts |
| 6,011,985 A | 1/2000 | Athan |
| 6,024,696 A | 2/2000 | Hoftman |
| 6,027,456 A | 2/2000 | Feler et al. |
| 6,038,469 A | 3/2000 | Karlsson et al. |
| 6,050,996 A | 4/2000 | Schmaltz |
| 6,074,343 A | 6/2000 | Nathanson |
| 6,083,154 A | 7/2000 | Liu |
| 6,099,468 A | 8/2000 | Santilli |
| 6,104,957 A | 8/2000 | Alo et al. |
| 6,132,387 A | 10/2000 | Gozani et al. |
| 6,213,940 B1 | 4/2001 | Sherts |
| 6,224,545 B1 | 5/2001 | Cocchia |
| 6,231,506 B1 | 5/2001 | Hu |
| 6,254,532 B1 | 7/2001 | Paolitto |
| 6,259,945 B1 | 7/2001 | Epstein et al. |
| 6,264,605 B1 | 7/2001 | Scirica |
| 6,266,558 B1 | 7/2001 | Gozani et al. |
| 6,273,853 B1 | 8/2001 | Cartier |
| 6,283,912 B1 | 9/2001 | Hu |
| 6,292,701 B1 | 9/2001 | Prass et al. |
| 6,306,100 B1 | 10/2001 | Prass |
| 6,322,500 B1 | 11/2001 | Sikora |
| 6,334,068 B1 | 12/2001 | Hacker |
| 6,340,345 B1 | 1/2002 | Lees |
| 6,393,325 B1 | 5/2002 | Mann et al. |
| 6,416,480 B1 | 7/2002 | Nenov |
| 6,425,859 B1 | 7/2002 | Foley et al. |
| 6,451,015 B1 | 9/2002 | Rittman et al. |
| 6,466,817 B1 | 10/2002 | Kaula et al. |
| 6,511,423 B2 | 1/2003 | Farley |
| 6,564,078 B1 | 5/2003 | Marino et al. |
| 6,685,632 B1 | 2/2004 | Hu |
| 6,712,795 B1 | 3/2004 | Cohen |
| 6,819,956 B2 | 11/2004 | DiLorenzo |
| 6,830,051 B1 | 12/2004 | Lesniak et al. |
| 6,837,851 B1 | 1/2005 | Valentini |
| 6,849,064 B2 | 2/2005 | Hamada |
| 6,895,280 B2 | 5/2005 | Meadows et al. |
| 6,926,728 B2 | 8/2005 | Zucherman et al. |
| 6,929,606 B2 | 8/2005 | Ritland |
| 6,945,933 B2 | 9/2005 | Branch |
| 6,951,538 B2 | 10/2005 | Ritland |
| 6,994,669 B1 | 2/2006 | Gannoe |
| 7,052,457 B2 | 5/2006 | Fanous |
| 7,089,059 B1 | 8/2006 | Pless |
| 7,135,020 B2 | 11/2006 | Lawes |
| 7,141,015 B2 | 11/2006 | Ruane |
| 7,160,298 B2 | 1/2007 | Lawes |
| 7,182,729 B2 | 2/2007 | Abdelgany |
| 7,207,949 B2 | 4/2007 | Miles et al. |
| 7,216,001 B2 | 5/2007 | Hacker et al. |
| 7,374,534 B2 | 5/2008 | Dalton |
| 7,435,219 B2 | 10/2008 | Kim |
| 7,470,236 B1 | 12/2008 | Kelleher et al. |
| 7,481,766 B2 | 1/2009 | Lee |
| 7,522,953 B2 | 4/2009 | Kaula et al. |
| 7,537,565 B2 | 5/2009 | Bass |
| 7,582,058 B1 | 9/2009 | Miles |
| 7,632,269 B2 | 12/2009 | Truckai |
| 7,641,659 B2 | 1/2010 | Emstad |
| 7,657,308 B2 | 2/2010 | Miles et al. |
| 7,664,544 B2 | 2/2010 | Miles et al. |
| 7,691,057 B2 | 4/2010 | Miles |
| 7,819,801 B2 | 10/2010 | Miles |
| 7,850,608 B2 | 12/2010 | Hamada |
| 7,905,840 B2 | 3/2011 | Pimenta |
| 7,920,922 B2 | 4/2011 | Gharib |
| 7,922,657 B2 | 4/2011 | Gillinov |
| 7,931,589 B2 | 4/2011 | Cohen |
| 7,931,591 B2 | 4/2011 | McCarthy |
| 7,946,982 B2 | 5/2011 | Hamada |
| 7,962,191 B2 | 6/2011 | Marino |
| 7,963,927 B2 | 6/2011 | Kelleher et al. |
| 7,976,463 B2 | 7/2011 | Dewey |
| 7,981,031 B2 | 7/2011 | Frasier |
| 8,068,912 B2 | 11/2011 | Kaula et al. |
| 8,100,828 B2 | 1/2012 | Frey |
| 8,137,284 B2 | 3/2012 | Miles |
| 8,152,714 B2 | 4/2012 | Garcia-Bengochea |
| 8,152,720 B2 | 4/2012 | Loftus |
| 8,206,293 B2 | 6/2012 | Reglos |
| 8,226,554 B2 | 7/2012 | McBride |
| 8,251,997 B2 | 8/2012 | Michelson |
| 8,255,045 B2 | 8/2012 | Gharib |
| 8,257,255 B2 | 9/2012 | Farley |
| 8,262,570 B2 | 9/2012 | White |
| 8,267,859 B2 | 9/2012 | Holmes |
| 8,287,597 B1 | 10/2012 | Pimenta |
| 8,313,430 B1 | 11/2012 | Pimenta |
| 8,328,851 B2 | 12/2012 | Curran |
| 8,343,163 B1 | 1/2013 | Arambula |
| 8,360,971 B2 | 1/2013 | Farley |
| 8,425,602 B2 | 4/2013 | Guyer |
| 8,449,463 B2 | 5/2013 | Nunley |
| 8,517,935 B2 | 8/2013 | Marchek |
| 8,562,621 B2 | 10/2013 | Mignucci |
| 8,568,306 B2 | 10/2013 | Hardenbrook |
| 8,636,655 B1 | 1/2014 | Childs |
| 8,636,656 B2 | 1/2014 | Nichter |
| 8,715,175 B2 | 5/2014 | Assaker |
| 8,790,406 B1 | 7/2014 | Smith |
| 8,821,394 B2 | 9/2014 | Hawkins |
| 8,821,396 B1 | 9/2014 | Miles |
| 8,852,090 B2 | 10/2014 | Friedrich |
| 8,876,687 B2 | 11/2014 | Jones |
| 8,876,904 B2 | 11/2014 | Pimenta |
| 8,882,661 B2 | 11/2014 | Hutton |
| 2001/0039949 A1 | 11/2001 | Loubser |
| 2002/0007129 A1 | 1/2002 | Marino |
| 2004/0181165 A1 | 9/2004 | Hoey |
| 2005/0159785 A1 | 7/2005 | Rueter |
| 2005/0182454 A1 | 8/2005 | Gharib et al. |
| 2006/0069315 A1* | 3/2006 | Miles et al. ............ 600/219 |
| 2006/0074278 A1 | 4/2006 | Petit |
| 2006/0166157 A1 | 7/2006 | Rahman et al. |
| 2006/0224044 A1 | 10/2006 | Marchek |
| 2007/0038033 A1 | 2/2007 | Jones |
| 2007/0156025 A1 | 7/2007 | Marchek |
| 2007/0208228 A1 | 9/2007 | Pavento |
| 2007/0290369 A1 | 12/2007 | Hasegawa |

(56) References Cited

U.S. PATENT DOCUMENTS

| | | |
|---|---|---|
| 2008/0064976 A1 | 3/2008 | Kelleher et al. |
| 2008/0064977 A1 | 3/2008 | Kelleher et al. |
| 2008/0167574 A1 | 7/2008 | Farquhar et al. |
| 2008/0183044 A1 | 7/2008 | Colleran |
| 2008/0183214 A1 | 7/2008 | Copp |
| 2008/0234550 A1 | 9/2008 | Hawkes |
| 2009/0018399 A1 | 1/2009 | Martinelli |
| 2009/0018610 A1 | 1/2009 | Gharib et al. |
| 2009/0062619 A1 | 3/2009 | Bjork |
| 2009/0069635 A1 | 3/2009 | Gephart |
| 2009/0076516 A1 | 3/2009 | Lowry |
| 2009/0105547 A1 | 4/2009 | Vayser |
| 2009/0177112 A1 | 7/2009 | Gharib et al. |
| 2009/0264710 A1 | 10/2009 | Chana |
| 2010/0160738 A1 | 6/2010 | Miles |
| 2010/0312068 A1 | 12/2010 | Dalton |
| 2011/0137130 A1 | 6/2011 | Thalgott |
| 2011/0144450 A1 | 6/2011 | Paolitto |
| 2011/0172494 A1 | 7/2011 | Bass |
| 2011/0224497 A1 | 9/2011 | Weiman |
| 2011/0237902 A1 | 9/2011 | Rosen |
| 2011/0301421 A1 | 12/2011 | Michaeli |
| 2011/0301422 A1 | 12/2011 | Woolley |
| 2011/0301423 A1 | 12/2011 | Koros |
| 2012/0046527 A1 | 2/2012 | Cianfrani |
| 2012/0083662 A1 | 4/2012 | Hamada |
| 2012/0130180 A1 | 5/2012 | Pell |
| 2012/0136392 A1 | 5/2012 | Keegan |
| 2012/0203070 A1 | 8/2012 | Crenshaw |
| 2012/0245431 A1 | 9/2012 | Baudouin |
| 2012/0245432 A1 | 9/2012 | Karpowicz |
| 2012/0283521 A1 | 11/2012 | Smith |
| 2012/0330106 A1 | 12/2012 | Wright |
| 2013/0123581 A1 | 5/2013 | Fritzinger |
| 2013/0158359 A1 | 6/2013 | Predick |
| 2013/0190575 A1 | 7/2013 | Mast |
| 2013/0261401 A1 | 10/2013 | Hawkins |
| 2014/0024900 A1 | 1/2014 | Capote |
| 2014/0066718 A1 | 3/2014 | Fiechter |
| 2014/0073857 A1 | 3/2014 | Dodson |
| 2014/0128979 A1 | 5/2014 | Womble |
| 2014/0135584 A1 | 5/2014 | Lee |

FOREIGN PATENT DOCUMENTS

| | | |
|---|---|---|
| DE | 4425652 | 2/1996 |
| EP | 0951868 | 10/1999 |
| EP | 1829488 | 9/2007 |
| JP | 3187929 | 12/2013 |
| WO | WO-9320741 | 10/1993 |
| WO | WO-03017847 | 3/2003 |
| WO | WO-2007002405 | 1/2007 |
| WO | WO-2010121291 | 10/2010 |
| WO | WO-2010125598 | 11/2010 |
| WO | WO-2010136860 | 12/2010 |
| WO | WO-2012093368 | 7/2012 |
| WO | WO-2013000105 | 1/2013 |

OTHER PUBLICATIONS

"Nerve Proximity and Status Detection System and Method," International Search Report from International Application No. PCT/US01/18606, Oct. 18, 2001, 6 pages.

"Relative Nerve Movement and Status Detection System and Method," International Search Report from International Application No. PCT/US01/18579, Jan. 15, 2002, 6 pages.

"System and Method for Determining Nerve Proximity Direction and Pathology During Surgery," International Search Report from International Application No. PCT/US02/22247, Mar. 27, 2003, 4 pages.

"System and Methods for Determining Nerve Direction to a Surgical Instrument," International Search Report from International Application No. PCT/US03/02056, Aug. 12, 2003, 5 pages.

"Systems and Methods for Performing Percutaneous Pedicle Integrity Assessments," International Search Report from International Application No. PCT/US02/35047, Aug. 11, 2003, 5 pages.

"Systems and Methods for Performing Surgery Procedures and Assessments," International Search Report from International Application No. PCT/US02/30617, Jun. 5, 2003, 4 pages.

"Systems and Methods for Performing Neurophysiologic Assessments During Spine Surgery," International Search Report from International Application No. PCT/US06/03966, Oct. 23, 2006, 5 pages.

"Multi-Channel Stimulation Threshold Detection Algorithm for Use in Neurophysiology Monitoring," International Search Report and Written Opinion from International Application No. PCT/US06/37013, Mar. 19, 2007, 10 pages.

"Surgical Access System and Related Methods," International Search Report and Written Opinion from International Application No. PCT/US2011/001489, mailed Dec. 13, 2011 (10 pages).

"Neurovision SE Nerve Locator/Monitor," RLN Systems Inc. Operator's Manual, 1999, 22 pages.

Calancie, et al., "Stimulus-Evoked EMG Monitoring During Transpedicular Lumbosacral Spine Instrumentation," Spine 1994, 19(24): 2780-2786.

Holland, et al., "Higher Electrical Stimulus Intensities are Required to Activate Chronically Compressed Nerve Roots. Implications for Intraoperative Electromyographic Pedicle Screw Testing," Spine 1998, 23(2): 224-227.

Bednarik, et al., "The Value of Somatosensory- and Motor-Evoked Potentials in Predicting and Monitoring the Effect of Therapy in Spondylotic Cervical Myelopathy," Spine 1999, 24(15):1593-1598.

Calancie, et al., "Threshold-level multipulse transcranial electrical stimulation of motor cortex for intraoperative monitoring of spinal motor tracts: description of method and comparison to somatosensory evoked potential monitoring," J Neurosurg 1998, 88:457-470.

Calancie, et al., "Threshold-level repetitive transcranial electrical stimulation for intraoperative monitoring of central motor conduction," J Neurosurg (Spine 1) 2011, 95:161-168.

Calancie and Molano, "Alarm Criteria for Motor-Evoked Potentials," Spine 2008 33(4):406-414.

Deletis, et al., "Neurophysiological mechanisms underlying motor evoked potentials in anesthetized humans. Part 1. Recovery time of corticospinal tract direct waves elicited by pairs of transcranial electrical stimuli," Clin Neurophysiol 2001, 112:438-444.

Deletis, et al., "Neurophysiological mechanisms underlying motor evoked potentials in anesthetized humans. Part 2. Relationship between epidurally and muscle recorded MEPs in man," Clin Neurophysiol 2001, 112:445-452.

Ginsburg, et al., "Postoperative paraplegia with preserved intraoperative somatosensory evoked potentials," J Neurosurg 1985, 63:296-300.

Gokaslan, et al., "Intraoperative Monitoring of Spinal Cord Function Using Motor Evoked Potentials via Transcutaneous Epidural Electrode During Anterior Cervical Spinal Surgery," J Spinal Disord 1997, 10(4):299-303.

Kombos, et al., "Monitoring of intraoperative motor evoked potentials to increase the safety of surgery in and around the motor cortex," J Neurosurg 2001, 95:608-614.

Langeloo, et al., "A New Application of TCE-MEP: Spinal Cord Monitoring in Patients With Severe Neuromuscular Weakness Undergoing Corrective Spine Surgery," J Spinal Disord 2001, 14(5):445-448.

Langeloo, et al., "Transcranial Electrical Motor-Evoked Potential Monitoring During Surgery for Spinal Deformity," Spine 2003, 28(10) 1043-1050.

MacDonald, "Safety of Intraoperative Transcranial Electrical Stimulation Motor Evoked Potential Monitoring," J Clin Neurophys 2002, 19(5):416-429.

Osburn, et al., "TCeMEPs offer Safe, Reliable Monitoring of Spinal Cord Motor Pathway Function during Cervical Procedures Performed for Post-traumatic Spine Injury," 17$^{th}$ Annual Meeting of the American Society of Neurophysiological Monitoring Abstract Presentations, 2006.

(56) References Cited

OTHER PUBLICATIONS

Osburn, "A Guide to the Performance of Transcranial Electrical Motor Evoked Potentials. Part 1. Basic Concepts, Recording Parameters, Special Consideration, and Application," Am J END Technol 2006, 46:98-158.

Watanabe, et al., "Transcranial electrical stimulation through screw electrodes for intraoperative monitoring of motor evoked potentials," J Neurosurg 2004, 100:155-160.

Wiedemayer, et al., "False negative findings in intraoperative SEP monitoring: analysis of 658 neurosurgical cases and review of published reports," J Neurol Neurosurg Psychiatry 2004, 75:280-286.

Balzer, et al., "Simultaneous Somatosensory Evoked Potential and Electromyographic Recordings during Lumbosacral Decompression and Instrumentation Technique Application," Neurosurgery 1998, 42:1318-1325.

Banoczi, "Update on Anesthetic and Metabolic Effects During Intraoperative Neurophysiological Monitoring (IONM)," Am J END Technol 2005, 45:225-239.

Chawla, et al., "Somatosensory Evoked Potentials: Clinical Applications," eMedicine Neurology, 2008, http://emedicine.medscape.com/article/1139393-overview.

Dawson, et al., "Spinal Cord Monitoring. Results of the Scoliosis Research Society and the European Spinal Deformity Society Survey," Spine 1991, 16(8) Supplement: S361-S364.

Deutsch, et al., "Somatosensory evoked potential monitoring in anterior thoracic vertebrectomy," J Neurosurg (Spine2) 2000, 92:155-161.

Devlin and Schwartz, "Intraoperative Neurophysiologic Monitoring During Spinal Surgery," J Am Acad Orthop Surg 2007, 15(9):549-560.

Gunnarsson, et al., "Real-Time Continuous Intraoperative Electromyographic and Somatosensory Evoked Potential Recordings in Spinal Surgery: Correlation of Clinical and Electrophysiologic Findings in a Prospective, Consecutive Series of 213 Cases," Spine 2004, 29(6):677-684.

Jones, et al., "Two cases of quadriparesis following anterior cervical discectomy, with normal perioperative somatosensory evoked potentials," J Neurol Neurosurg Psychiatry 2003, 74:273-276.

Kamel, et al., "The Use of Somatosensory Evoked Potentials to Determine the Relationship Between Pateint Positioning and Impending Upper Extremity Nerve Injury During Spine Surgery: A Retrospective analysis," International Anesthesia Research Society 2006, 102:1538-1542.

Kombos, et al., "Impact of Somatosensory Evoked Potential Monitoring on Cervical Surgery," J Clin Neurophys 2003, 20(2): 122-128.

Kraft, et al., "Somatosensory Evoked Potentials: Clinical Uses," Muscle Nerve 1998, 21:252-258.

Legatt and Soliman, "Somatosensory Evoked Potentials: General Principles," eMedicine Neurology, 2006, http://emedicine.medscape.com/article/1139906-overview.

More, et al., "Cortical Evoked Potential Monitoring During Spinal Surgery: Sensitivity, Specificity, Reliability, and Criteria for Alarm," J Spinal Disord 1988, 1(1):75-80.

Nash, et al., "Spinal Cord Monitoring During Operative Treatment of the Spine," Clin Orthop Relat Res 1977, 126:100-105.

Nuwer, et al., "Somatosensory evoked potential spinal cord monitoring reduces neurologic deficits after scoliosis surgery: results of a large multicenter survey," Electroencephalogr Clin Neurophysiol 1995, 96:611.

Padberg, et al., "Somatosensory- and Motor-Evoked Potential Monitoring Without a Wake-Up Test During Idiopathic Scoliosis Surgery: An Accepted Standard of Care," Spine 1998, 23(12):1392-1400.

Pelosi, et al., "Combined monitoring or motor and somatosensory evoked potentials in orthopaedic spinal surgery," Clin Neurophysiol 2002, 113:1082-1091.

Sloan and Heyer, "Anesthesia for Intraoperative Neurophysiologic Monitoring of the Spinal Cord," J Clin Neurophys 2002, 19(5):430-443.

Toleikis, "Intraoperative Monitoring Using Somatosensory Evoked Potentials," J Clin Monit Comput 2005, 19:241-258.

Wiedemayer, et al., "The impact of neurophysiological intraoperative monitoring on surgical decisions: a critical analysis of 423 cases," J Neurosurg 2002, 96:255-262.

Zornow and Drummond, "Intraoperative Somatosensory Evoked Responses Recorded During Onset of the Anterior Spinal Artery Syndrome," J Clin Monit 1989, 5:243-245.

Bendersky, et al. "Monitoring lumbar plexus integrity in extreme lateral transpsoas approaches to the lumbar spine: a new protocol with anatomical bases," Eur Spine J 2015, published online, DOI 10.1007/s00586-015-3801-9.

Silverstein, et al., "Saphenous Nerve Somatosensory Evoked Potentials: A Novel Technique to Monitor the Femoral Nerve During Transpsoas Lumbar Lateral Interbody Fusion," Spine 2014, 39(15)1254-1260.

Taylor, et al. "Chapter 5: The Role of Integrated Neurophysiologic Monitoring in XLIF®," eXtreme Lateral Interbody Fusion (XLIF®), 2' Ed., edited by J. Allan Goodrich, Ildemaro J. Volcan, 2013, pp. 45-57, Quality Medical Publishing, Inc., St. Louis, MO.

Uribe, et al., "Electromyographic Monitoring and Its Anatomical Implications in Minimally Invasive Spine Surgery," Spine 2010, 35(26S)S368-S374.

\* cited by examiner

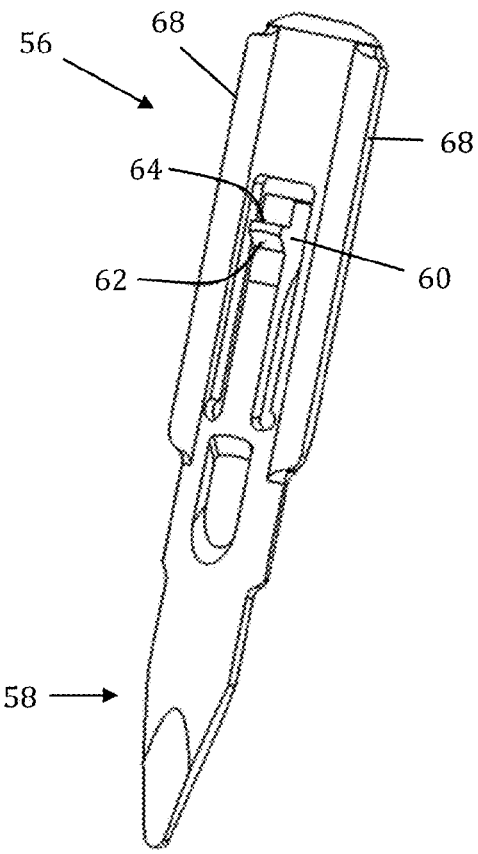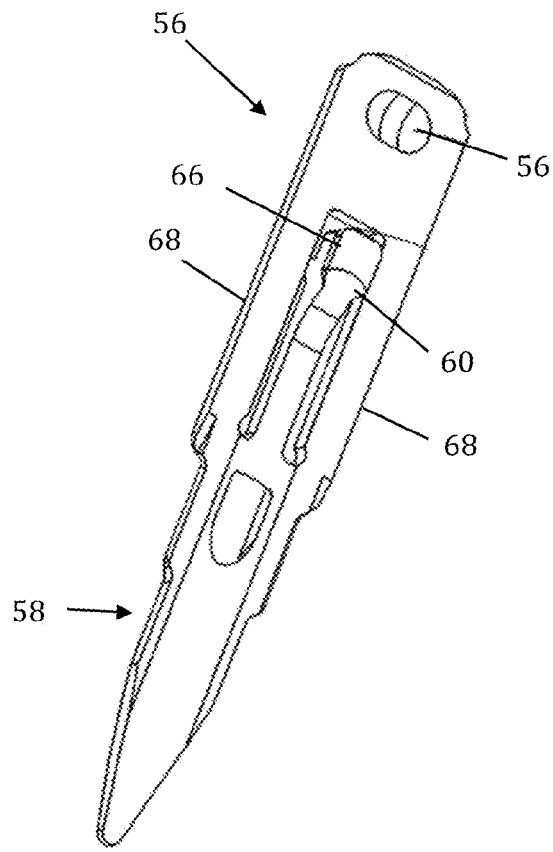
Fig. 4  Fig. 5
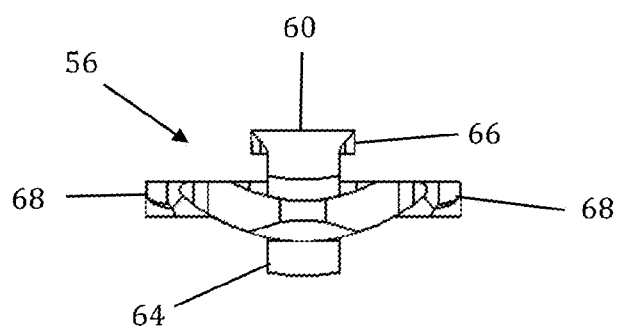
Fig. 6

SYSTEMS AND METHODS FOR PERFORMING NEUROPHYSIOLOGIC MONITORING DURING SPINE SURGERY

CROSS-REFERENCES TO RELATED APPLICATIONS

This non-provisional application claims priority under 35 U.S.C. 119(e) from U.S. Provisional Application Ser. No. 61/595,627 filed Feb. 6, 2012, the complete disclosure of which is hereby incorporated by reference into this application as if set forth fully herein. The present application incorporates by reference commonly owned and co-pending International Patent Application No. PCT/US01/01489, filed Aug. 8, 2011 and entitled "Surgical Access System and Related Methods," and commonly owned U.S. Pat. No. 8,255,045, issued Aug. 28, 2012 and entitled "Neurophysiology Monitoring System," the entire contents of each of which are hereby incorporated by reference into this disclosure as if set forth fully herein.

FIELD

This disclosure relates to a surgical retraction system and related instrumentation and methods for accessing a surgical target site for the purpose of performing surgical procedures.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylothesis (forward displacement of one vertebra over another), and other disorders caused by abnormalities, disease or trauma, such as ruptured or slipped discs, degenerative disc disease, fractured vertebra and the like. Patients that suffer from such conditions usually experience extreme and debilitating pain, as well as diminished nerve function.

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly high amounts of pain, lengthened hospitalization (increasing health care costs), and high morbidity in the patient population. Less-invasive surgical techniques (including so-called "minimal access" and "minimally invasive" techniques are gaining favor due to the fact that they involve accessing the surgical target site via incisions of substantially smaller size with greatly reduced tissue displacement requirements. This, in turn, reduces the pain, morbidity, and cost associated with such procedures. One such minimally invasive approach, a lateral trans-psoas approach to the spine, developed by NuVasive®, Inc., San Diego, Calif. (XLIF®) has demonstrated great success in reducing patient morbidity, shortening the duration of hospitalization, and speeding recovery time if it is employed.

To create the lateral access corridor to the lumbar spine, the patient is positioned on his or her side and a surgical access system is advanced through an incision, into the retroperitoneal space, and then through the psoas muscle until the target spinal site (for example, a disc space between a pair of adjacent vertebral bodies) is reached. The surgical access system may include a sequential dilation assembly of increasing diameter and a tissue retraction assembly. The sequential dilation assembly is advanced to the target site first and the retractor assembly is then advanced to the target site over the sequential dilation system. Stimulating electrodes may be provided on the distal tip of one or more of the different components of the surgical access system. Nerve monitoring may be performed while advancing one or more components of the dilation and retraction assemblies to the target site to detect the presence of, and thereby avoid, nerves lying in the trans-psoas path to the target site.

Once the retractor assembly has been docked at a target site however, a nerve situated near any location along the length of a retractor blade (for example, a center (posterior) blade) might come into inadvertent contact with the blade which could cause the nerve to become compressed over the course of the surgical procedure. As such, information regarding the depth, proximity, health, and status of nearby nerves during maintenance of a lateral access corridor is desirable. Because an at-risk nerve may not be in close proximity to the stimulating electrode on the distal tip of the retractor blade, large amounts of stimulation current could be required to depolarize the nerve and elicit a response though it is generally preferable to conduct the monitoring with the least intense stimulation necessary. Additionally, if a nerve is compressed, the closer the stimulation signal is delivered to the nerve the more precise information regarding the health and/or status of the nerve is likely to be. Furthermore, information regarding the depth of a nerve during maintenance of the lateral access corridor is also desirable, because it provides specific information as to the site of possible compression relative to the blade. Information regarding the status of the femoral nerve is also difficult to obtain because it is largely a sensory nerve.

SUMMARY

The present disclosure accomplishes this goal by providing a novel access system and related methods which involve detecting the existence of (and optionally the distance and/or direction to) neural structures before, during, and after the establishment of an operative corridor through (or near) any of a variety of tissues having such neural structures which, if contacted or impinged, may otherwise result in neural impairment for the patient. It is expressly noted that, although described herein largely in terms of use in spinal surgery, the access system of the present disclosure is suitable for use in any number of additional surgical procedures wherein tissue having significant neural structures must be passed through (or near) in order to establish an operative corridor. It is also expressly noted that, although shown and described herein largely within the context of lateral surgery in the lumbar spine, the access system of the present disclosure may be employed in any number of other spine surgery access approaches, including but not limited to posterior, postero-lateral, anterior, and antero-lateral access, and may be employed in the lumbar, thoracic and/or cervical spine, all without departing from the present disclosure.

According to one broad aspect of the present disclosure, the access system comprises a tissue distraction assembly and a tissue retraction assembly, both of which may be equipped with one or more electrodes for use in detecting the existence of (and optionally the distance and/or direction to) neural structures. The tissue distraction assembly (in conjunction with one or more elements of the tissue retraction assembly) is capable of, as an initial step, distracting a region of tissue between the skin of the patient and the surgical target site. The tissue retraction assembly is capable of, as a secondary step, being introduced into this distracted region to thereby define and establish the operative corridor. Once established, any of a variety of surgical instruments, devices, or implants may be passed through and/or manipulated within the operative corridor depending upon the given surgical procedure. The electrode(s) are capable of, during both tissue distraction and retraction, detecting the existence of (and optionally the distance and/or direction to) neural structures such that the operative corridor may be established through (or near) any of a variety of tissues having such neural structures which, if contacted or impinged, may otherwise result in neural impairment for the patient. In this fashion, the access system of the present disclosure may be used to traverse tissue that would ordinarily be deemed unsafe or undesirable, thereby broadening the number of manners in which a given surgical target site may be accessed.

The tissue distraction assembly may include any number of components capable of performing the necessary distraction. By way of example only, the tissue distraction assembly may include a K-wire and one or more dilators (e.g., sequentially dilating cannulae) for performing the necessary tissue distraction to receive the remainder of the tissue retractor assembly thereafter. One or more electrodes may be provided on one or more of the K-wire and dilator(s) to detect the presence of (and optionally the distance and/or direction to) neural structures during tissue distraction.

The tissue retraction assembly may include any number of components capable of performing the necessary retraction. By way of example only, the tissue retraction assembly may include one or more retractor blades extending from a handle assembly. The handle assembly may be manipulated to open the retractor assembly; that is, allowing the retractor blades to separate from one another (simultaneously or sequentially) to create an operative corridor to the surgical target site. In a preferred embodiment, this is accomplished by maintaining a posterior retractor blade in a fixed position relative to the surgical target site (so as to avoid having it impinge upon any exiting nerve roots near the posterior elements of the spine) while the additional retractor blades (i.e. cephalad-most and caudal-most blades) are moved or otherwise translated away from the posterior retractor blade (and each other) so as to create the operative corridor in a fashion that doesn't impinge upon the region of the exiting nerve roots. In one optional aspect of the present disclosure, the cephalad-most and/or caudal-most blades may pivot or rotate outward from a central axis of insertion, such that the operative corridor may be further expanded. In a further optional aspect of the present disclosure, the retractor may include a locking element to maintain the blades in an initial alignment during insertion, and a variable-stop mechanism to allow the user to control the degree of expansion of the operative corridor. A blade expander tool may be provided to facilitate manual pivoting of the retractor blades.

The retractor blades may be optionally dimensioned to receive and direct a locking shim element to augment the structural stability of the retractor blades and thereby ensure the operative corridor, once established, will not decrease or become more restricted, such as may result if distal ends of the retractor blades were permitted to "slide" or otherwise move in response to the force exerted by the displaced tissue. In a preferred embodiment, only the posterior retractor blade is equipped with such a rigid shim element. In an optional aspect, this shim element may be advanced into the disc space after the posterior retractor blade is positioned, but before the retractor is opened into the fully retracted position. The rigid shim element is preferably oriented within the disc space such that is distracts the adjacent vertebral bodies, which serves to restore disc height. It also preferably advances a sufficient distance within the disc space (preferably past the midline), which advantageously forms a protective barrier that prevents the migration of tissue (such as nerve roots) into the operative field and the inadvertent advancement of instruments outside the operative field. In an optional embodiment, the caudal-most and/or cephalad-most blades may be fitted with any number of retractor extenders for extending (laterally or length-wise) the blades, which advantageously forms a protective barrier that prevents the migration of tissue (such as muscle and soft tissue) into the operative field and the inadvertent advancement of instruments outside the operative field.

The retractor blades may optionally be equipped with a mechanism for transporting or emitting light at or near the surgical target site to aid the surgeon's ability to visualize the surgical target site, instruments and/or implants during the given surgical procedure. According to one embodiment, this mechanism may comprise, but need not be limited to, coupling one or more light sources to the retractor blades such that the terminal ends are capable of emitting light at or near the surgical target site. According to another embodiment, this mechanism may comprise, but need not be limited to, constructing the retractor blades of suitable material (such as clear polycarbonate) and configuration such that light may be transmitted generally distally through the walls of the retractor blade light to shine light at or near the surgical target site. This may be performed by providing the retractor blades having light-transmission characteristics (such as with clear polycarbonate construction) and transmitting the light almost entirely within the walls of the retractor blade (such as by frosting or otherwise rendering opaque portions of the exterior and/or interior) until it exits a portion along the interior (or medially-facing) surface of the retractor blade to shine at or near the surgical target site. The exit portion may be optimally configured such that the light is directed towards the approximate center of the surgical target site and may be provided along the entire inner periphery of the retractor blade or one or more portions therealong.

A neuromonitoring system such as the one shown and described in the above-mentioned '045 patent (incorporated by reference) may perform nerve proximity testing on one or more nerves of interest to ensure safe and reproducible access to a surgical target site and maintenance of the lateral access corridor. According to a first broad aspect of the present disclosure, the depth of a nerve of interest relative to a component of the surgical access assembly is localized, preferably prior to retraction of tissue from the lateral access corridor. According to a second broad aspect, the nerve of interest is stimulated at a location distal to the site of retraction and a response is recorded from a location proximal to the site of retraction. According to a third broad aspect, neurophysiologic responses across the site of retraction are recorded at multiple time points during a surgical procedure and are compared to previous responses. Changes in the neurophysiologic responses over time may provide useful information as to the health and status of the nerve.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIGS. 4-5 are front perspective and back perspective views, respectively, of one example of a locking shim forming part of the surgical access system of the present disclosure;

FIG. 6 is a top view of the locking shim of FIG. 4;

DESCRIPTION OF THE PREFERRED EMBODIMENT

Figure 1:
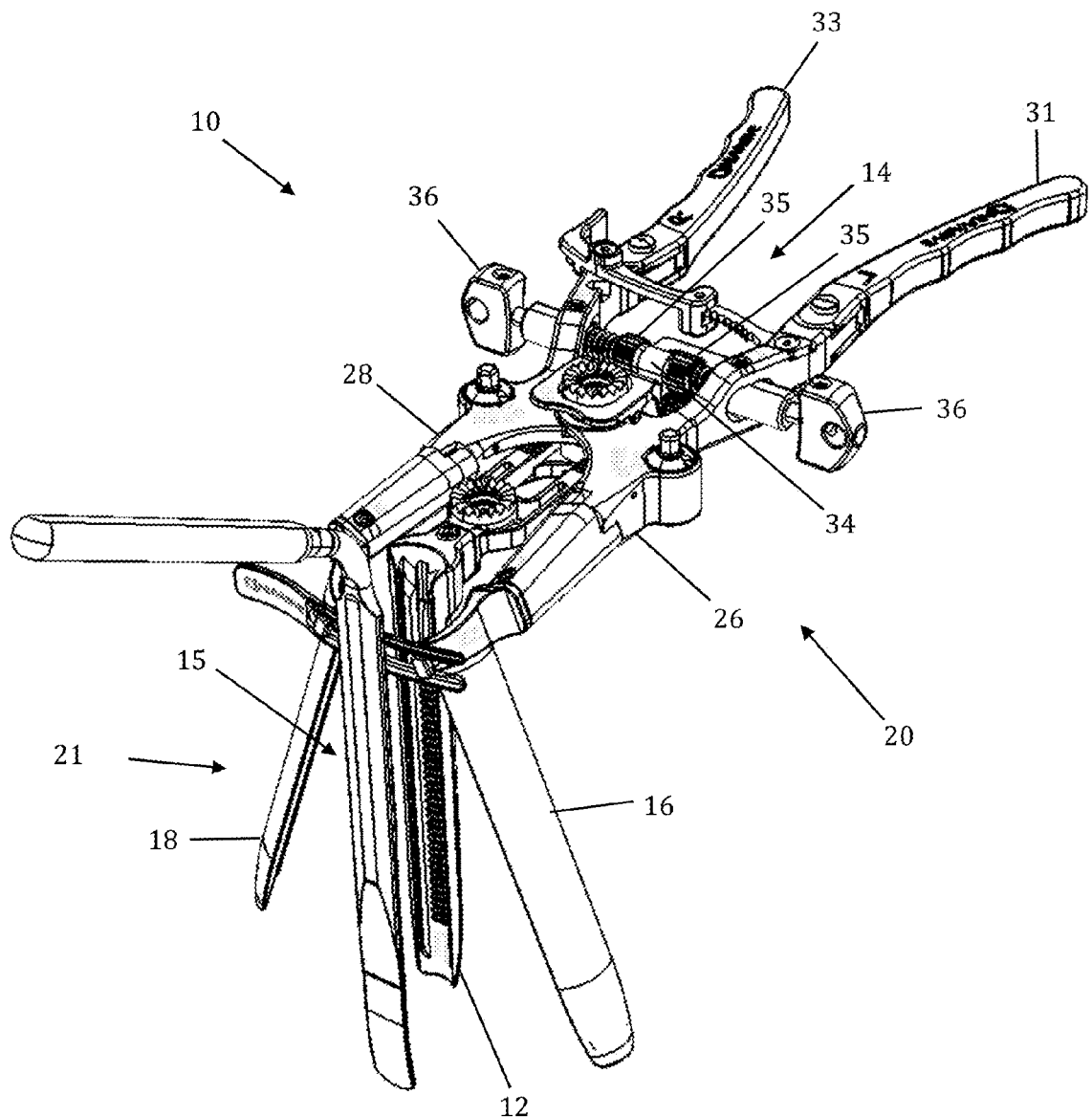
FIG. 1 is a perspective view of one example of a tissue retraction assembly forming part of a surgical access system according to one embodiment of the present disclosure, shown in a fully retracted or "open" position.

Illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. It is furthermore to be readily understood that, although discussed below primarily within the context of spinal surgery, the surgical access system of the present disclosure may be employed in any number of anatomical settings to provide access to any number of different surgical target sites throughout the body. It is also expressly noted that, although shown and described herein largely within the context of lateral surgery in the lumbar spine, the access system of the present disclosure may be employed in any number of other spine surgery access approaches, including but not limited to posterior, postero-lateral, anterior, and antero-lateral access, and may be employed in the lumbar, thoracic and/or cervical spine, all without departing from the present disclosure. The surgical access system disclosed herein boasts a variety of inventive features and components that warrant patent protection, both individually and in combination.

The present disclosure involves accessing a surgical target site in a fashion less invasive than traditional "open" surgeries and doing so in a manner that provides access in spite of the neural structures required to be passed through (or near) in order to establish an operative corridor to the surgical target site. Generally speaking, the surgical access system of the present disclosure accomplishes this by providing a tissue distraction assembly and a tissue retraction assembly, both of which may be equipped with one or more electrodes for use in detecting the existence of (and optionally the distance and/or direction to) neural structures.

These electrodes are preferably provided for use with a nerve surveillance system such as, by way of example, the type shown and described in the above referenced '045 patent. Generally speaking, this nerve surveillance system is capable of detecting the existence of (and optionally the distance and/or direction to) neural structures during the distraction and retraction of tissue by detecting the presence of nerves by applying a stimulation signal to such instruments and monitoring the evoked EMG signals from the myotomes associated with the nerves being passed by the distraction and retraction systems of the present disclosure. In so doing, the system as a whole (including the surgical access system of the present disclosure) may be used to form an operative corridor through (or near) any of a variety of tissues having such neural structures, particularly those which, if contacted or impinged, may otherwise result in neural impairment for the patient. In this fashion, the access system of the present disclosure may be used to traverse tissue that would ordinarily be deemed unsafe or undesirable, thereby broadening the number of manners in which a given surgical target site may be accessed.

Additionally, the neuromonitoring system may perform neuromonitoring as the retractor assembly is used to maintain the lateral access corridor as the target site is operated on. Such monitoring may be used to localize the depth of the nearby nerves relative to the length of a one or more blade and monitor the health and status of the nerves in closest proximity to that blade (or blades). As will be described in greater detail below, the retraction assembly of the surgical access system may be configured to: (1) localize the depth of nearby neural structures relative to one or more of the blades; (2) optimize a stimulating and/or recording location relative to one or more of the blades; (3) perform evoked EMG monitoring on the nerve or nerves in closest proximity to the blades; and (4) perform evoked sensory monitoring on the nerves in closest proximity to the blades. Aspects of the neuromonitoring systems used to facilitate performance of these functions are also described in the following commonly owned patent applications, collectively referred to as the "Neuromonitoring PCT Applications," the entire contents of each of which are hereby incorporated by reference as if set forth fully herein: U.S. Pat. No. 8,068,912, entitled "System and Methods for Determining Nerve Proximity, Direction, and Pathology During Surgery," filed on Jan. 9, 2004; U.S. Pat. No. 7,522,953, entitled "System and Methods for Performing Surgical Procedures and Assessments," filed on Mar. 25, 2004; U.S. Pat. No. 7,905,840, entitled Surgical Access System and Related Methods," filed Oct. 18, 2004; and U.S. Pat. No. 8,255,045, entitled "Neurophysiologic Monitoring System," filed on Apr. 4, 2008.

The tissue distraction assembly of the present disclosure, including a plurality of sequential dilators and a k-wire, is employed to distract the tissues extending between the skin of the patient and a given surgical target site (preferably along the posterior region of the target intervertebral disc). Once distracted, the resulting void or distracted region within the patient is of sufficient size to accommodate a tissue retraction assembly of the present disclosure. More specifically, the tissue retraction assembly (comprising a plurality of retractor blades extending from a handle assembly) may be advanced, with the blades in a first generally closed position, over the exterior of the outer dilator. At that point, the handle assembly may be operated to move the retractor blades into a second, open or "retracted" position to create an operative corridor to the surgical target site.

According to one aspect of the disclosure, following (or before) this retraction, a posterior shim element (which is preferably slidably engaged with the posterior retractor blade) may be advanced such that a distal shim extension is positioned within the posterior region of the disc space. If done before retraction, this helps ensure that the posterior retractor blade will not move posteriorly during the retraction process, even though the other retractor blades (e.g. cephalad-most and caudal-most) are able to move and thereby create an operative corridor. Fixing the posterior retractor blade in this fashion serves several important functions. First, the distal end of the shim element serves to distract the adjacent vertebral bodies, thereby restoring disc height. It also rigidly couples the posterior retractor blade in fixed relation relative to the vertebral bodies. The posterior shim element also helps ensure that surgical instruments employed within the operative corridor are incapable of being advanced outside the operative corridor, preventing inadvertent contact with the exiting nerve roots during the surgery. Once in the appropriate retracted state, the cephalad-most and caudal-most retractor blades may be locked in position and, thereafter, retractor extenders advanced therealong to prevent the ingress or egress of instruments or biological structures (e.g. nerves, vasculature, etc.) into or out of the operative corridor. Optionally, the cephalad-most and/or caudal-most retractor blades may be pivoted in an outward direction to further expand the operative corridor. Once the operative corridor is established, any of a variety of surgical instruments, devices, or implants may be passed through and/or manipulated within the operative corridor depending upon the given surgical procedure.

Figure 2:
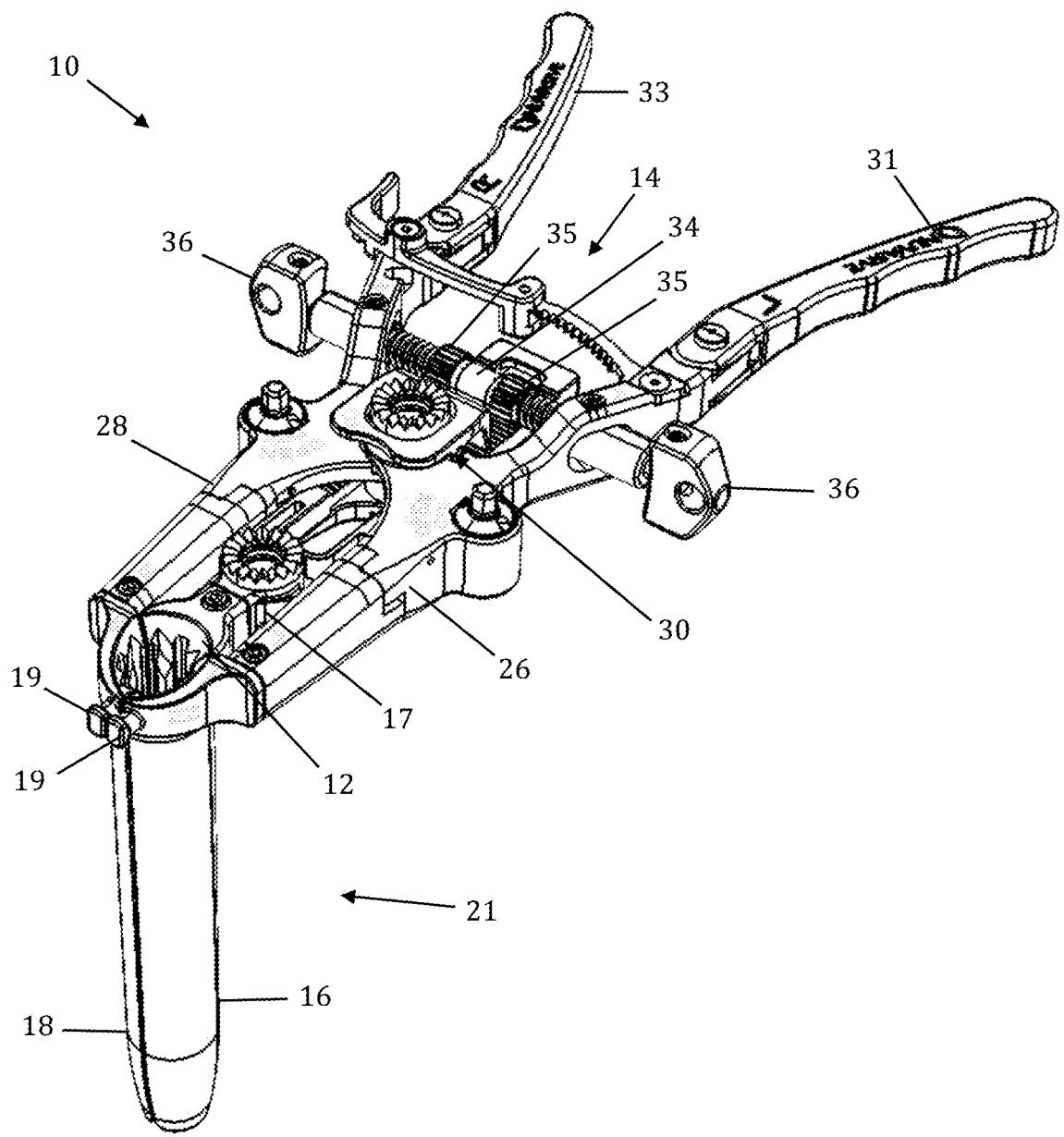
FIG. 2 is a perspective view of the tissue retraction assembly of FIG. 1 shown in a fully closed position.
Figure 3:
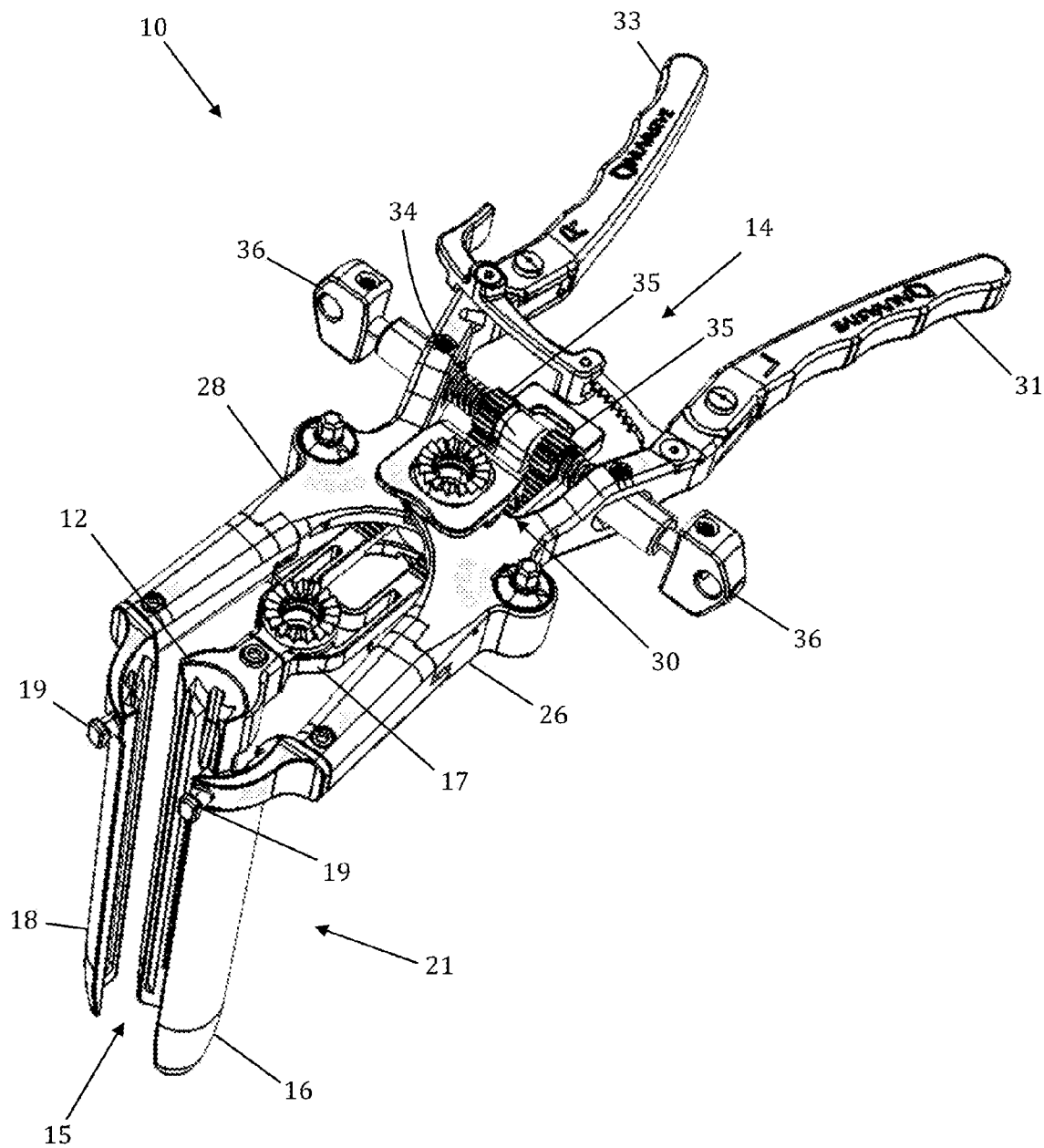
FIG. 3 is a perspective view of the tissue retraction assembly of FIG. 1 shown in a partially open position according to the present disclosure.

FIGS. 1-3 illustrate a tissue retraction assembly 10 forming part of a surgical access system according to the present disclosure, including a plurality of retractor blades 12, 16, 18 extending from a handle assembly 20. By way of example only, the handle assembly 20 is provided with a first retractor blade 12, a second retractor blade 16, and a third retractor blade 18. FIG. 1 illustrates the tissue retraction assembly 10 in a fully retracted or "open" configuration, with the retractor blades 12, 16, 18 positioned a distance from one another so as to form an operative corridor 15 therebetween which extends to a surgical target site (e.g. an annulus of an intervertebral disc). In an important aspect of the present disclosure, the blades 16, 18 are capable of being pivoted or rotated relative to the handle 20, as best appreciated with combined reference to FIGS. 1 & 2. FIG. 2 shows the tissue retraction assembly 10 in an initial "closed" configuration, with the retractor blades 12, 16, 18 generally abutting one another. FIG. 3 shows the tissue retraction assembly 10 in a "partially open" configuration. Although shown and described below with regard to the three-fixed-bladed configuration, it is to be readily appreciated that the number of retractor blades may be increased or decreased without departing from the scope of the present disclosure. Moreover, although described and shown herein with reference to a generally lateral approach to a spinal surgical target site (with the first blade 12 being the "posterior" blade, the second blade 16 being the "cephalad-most" blade, and the third blade 18 being the "caudal-most" blade), it will be appreciated that the tissue retraction assembly 10 of the present disclosure may find use in any number of different surgical approaches, including generally posterior, generally postero-lateral, generally anterior and generally antero-lateral.

The handle assembly 20 may be coupled to any number of mechanisms for rigidly registering the handle assembly 20 in fixed relation to the operative site, such as through the use of an articulating arm mounted to the operating table (not shown). The handle assembly 20 includes first and second arm members 26, 28 hingedly coupled via coupling mechanism shown generally at 30. The second retractor blade 16 is rigidly coupled (generally perpendicularly) to the end of the first arm member 26. The third retractor blade 18 is rigidly coupled (generally perpendicularly) to the end of the second arm member 28. The first retractor blade 12 is rigidly coupled (generally perpendicularly to) a translating member 17, which is coupled to the handle assembly 20 via a linkage assembly shown generally at 14. The linkage assembly 14 includes a roller member 34 having a pair of manual knob members 36 which, when rotated via manual actuation by a user, causes teeth 35 on the roller member 34 to engage within ratchet-like grooves 37 in the translating member 17. Thus, manual operation of the knobs 36 causes the translating member 17 to move relative to the first and second arm members 26, 28.

Through the use of handle extenders 31, 33, the arms 26, 28 may be simultaneously opened such that the second and third retractor blades 16, 18 move away from one another. In this fashion, the dimension and/or shape of the operative corridor 15 may be tailored depending upon the degree to which the translating member 17 is manipulated relative to the arms 26, 28. That is, the operative corridor 15 may be tailored to provide any number of suitable cross-sectional shapes, including but not limited to a generally circular cross-section, a generally ellipsoidal cross-section, a generally triangular cross-section, and/or an oval cross-section. Optional light emitting devices (not shown) may be coupled to one or more of the retractor blades 12, 16, 18 to direct light down the operative corridor 15.

The retractor blades 12, 16, 18 may be composed of any material suitable for introduction into the human body, including but not limited to aluminum, titanium, and/or clear polycarbonate, that would ensure rigidity during tissue distraction. The retractor blades 12, 16, 18 may be optionally coated with a carbon fiber reinforced coating to increase strength and durability. The retractor blades 12, 16, 18 may be optionally constructed from partially or wholly radiolucent materials (e.g. aluminum, PEEK, carbon-fiber, and titanium) to improve the visibility of the surgeon during imaging (e.g. radiographic, MRI, CT, fluoroscope, etc.). The retractor blades 12, 16, 18 may be provided in any number of suitable lengths, depending upon the anatomical environment and surgical approach, such as (for example) the range from 20 mm to 150 mm. Based on this range of sizes, the tissue retraction assembly 10 of the present disclosure is extremely versatile and may be employed in any of a variety of desired surgical approaches, including but not limited to lateral, posterior, postero-lateral, anterior, and antero-lateral, by simply selecting the desired size retractor blades 12, 16, 18 and attaching them to the handle assembly 20 as will be described herein.

Figure 11:
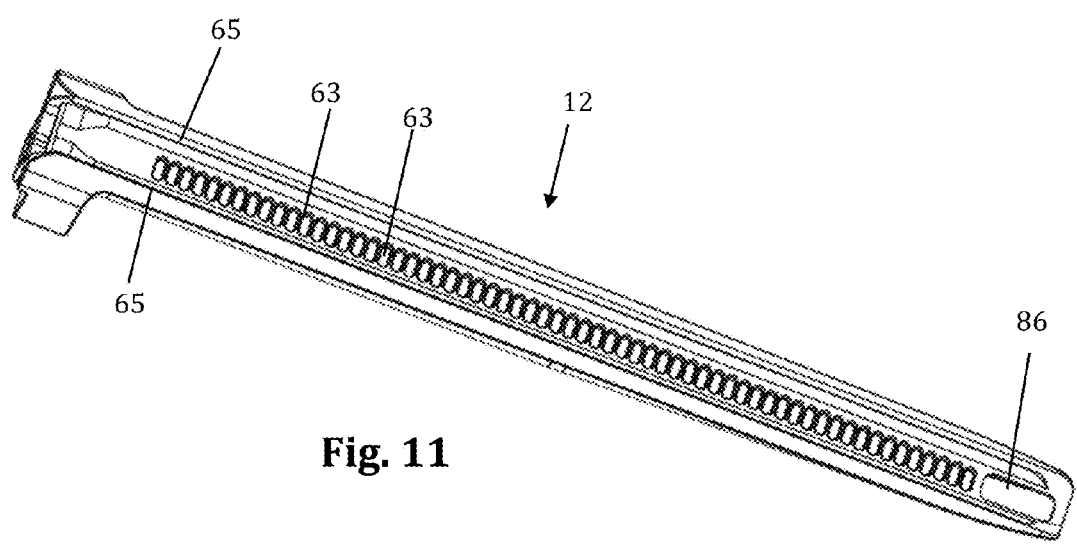
Figure 12:
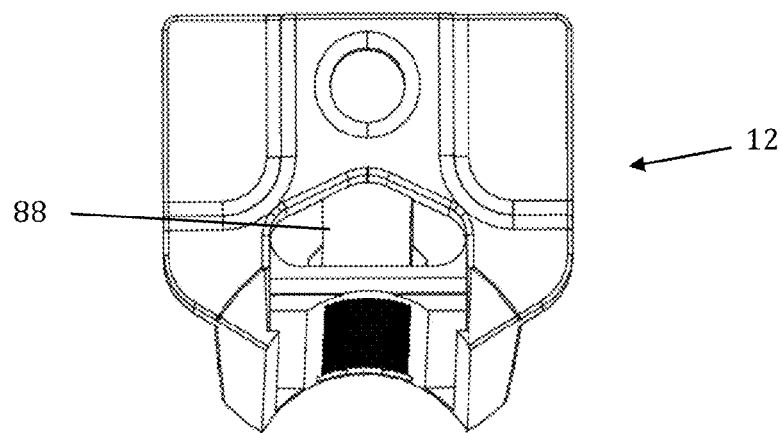
FIG. 12 is top perspective view of the retractor blade of FIG. 10.

The retractor blades 12, 16, 18 may be equipped with various additional features or components. By way of example only, one or more of the retractor blades 12, 16, 18 may be equipped with a shim, such as a locking shim 56 as shown in FIGS. 4-6. In a preferred embodiment, the intradiscal locking shim 56 is suitable for engagement with the posterior blade 12. However, it should be noted that any shim 56 may be used with any blade 12, 16, 18 without departing from the scope of the present disclosure. The locking intradiscal shim 56 has a distal tapered region 58 which may be advanced into the disc space for the purpose of distracting the adjacent vertebral bodies (thereby restoring disc height) and/or anchoring the blade 12 relative to the spine. The locking intradiscal shim 56 also forms a protective barrier to prevent the ingress or egress of instruments or biological structures (e.g. nerves, vasculature, etc.) into or out of the operative corridor 15. The locking intradiscal shim 56 locks in position on the retractor blade 12 to prevent the shim from dislodging and allowing the retractor to move from the targeted location. To lock position on the blade, the shim 56 has a flexible engagement tab 60 with a ramped leading edge 62 that allows it to advance down indentations 63 on the inner surface of the retractor blade 12 (FIG. 11). The trailing edge 64 of the engagement tab 60 is squared to prevent disengagement (thus preventing unwanted backout of the shim) from the indentation 63 without use of a removal tool (not shown). The engagement tab 60 also includes a T-shaped removal lip 66 configured to engage a shim removal tool, an example of which is shown and described in PCT App. No. PCT/US01/01489 (incorporated by reference). The T-shaped lip 66 of the engagement tab 60 allows the removal tool to lift the trailing edge 64 away from the retractor blade 12 and remove the shim 56. The locking intradiscal shim 56 has a pair of elongated tab members 68 that are configured to slideably engage elongated slot members 65 that run the length of the inside surface of the retractor blade 12 (FIG. 11). The locking intradiscal shim 56 includes a dimple or aperture 56 located near the proximal end of the shim 56 configured for engagement with a shim removal tool.

The locking intradiscal shim 56 may be made from any material suitable for use in the human body, including but not limited to biologically compatible plastic and/or metal, preferably partially or wholly radiolucent in nature material (such as aluminum, PEEK, carbon-fibers and titanium). The intradiscal shim 56 may also be coated with an insulative coating (e.g. a parylene coating) to prevent current shunting or density changes from electrodes situated at the distal end of the retractor blade 12. The shim element 56 may be composed of a material that would destruct when autoclaved (such as polymer containing a portion of glass particles), which may be advantageous in preventing the unauthorized re-use of the shim element 56 (which would be provided to the user in a sterile state).

According to the present disclosure, the locking intradiscal shim 56 may be provided with one or more electrodes (e.g. at or near their distal regions) equipped for use with a neuromonitoring system. Such a neuromonitoring system may be capable of detecting the existence of (and optionally the distance and/or direction to) neural structures during the retraction of tissue by detecting the presence of nerves by applying a stimulation signal to the electrodes and monitoring the evoked EMG signals from the myotomes associated with the nerves in the vicinity of the tissue retraction system 10 of the present disclosure. In so doing, the system as a whole (including the tissue retraction system 10 of the present disclosure) may be used to form an operative corridor through (or near) any of a variety of tissues having such neural structures, particularly those that, if contacted or impinged, may otherwise result in neural impairment for the patient. In this fashion, the access system of the present disclosure may be used to traverse tissue that would ordinarily be deemed unsafe or undesirable, thereby broadening the number of manners in which a given surgical target site may be accessed.

As mentioned above, a nerve monitoring system may be provided for use with the tissue retraction assembly. According to one example, the nerve monitoring component of the retractor system is the posterior retractor blade 12, which may be made of a conductive material (e.g. aluminum) and coated with a insulative coating to direct stimulation from the nerve monitoring system to the tissue adjacent the distal end. According to another example embodiment, pictured in FIGS. 8-16, the neuromonitoring feature of the tissue retraction assembly includes two main components: a center (posterior) blade that forms part of a tissue retraction assembly 10 and an electrode body 70. For example, the electrode body 70 shown and described is slideably coupled to the posterior blade 12. By way of further example, the electrode body 70 shown is disposable. A clip cable 72 may be used to connect the electrode body 70 to the neuromonitoring system. One potential advantage of the electrode body 70 and accompanying posterior blade 12 is the increased ability to attain consistent and repeatable neuromonitoring functionality throughout the course of a single surgery and from surgery to surgery (since there is no risk of erosion of the insulative coating on the blade which can lead to current shunting).

Figure 7:
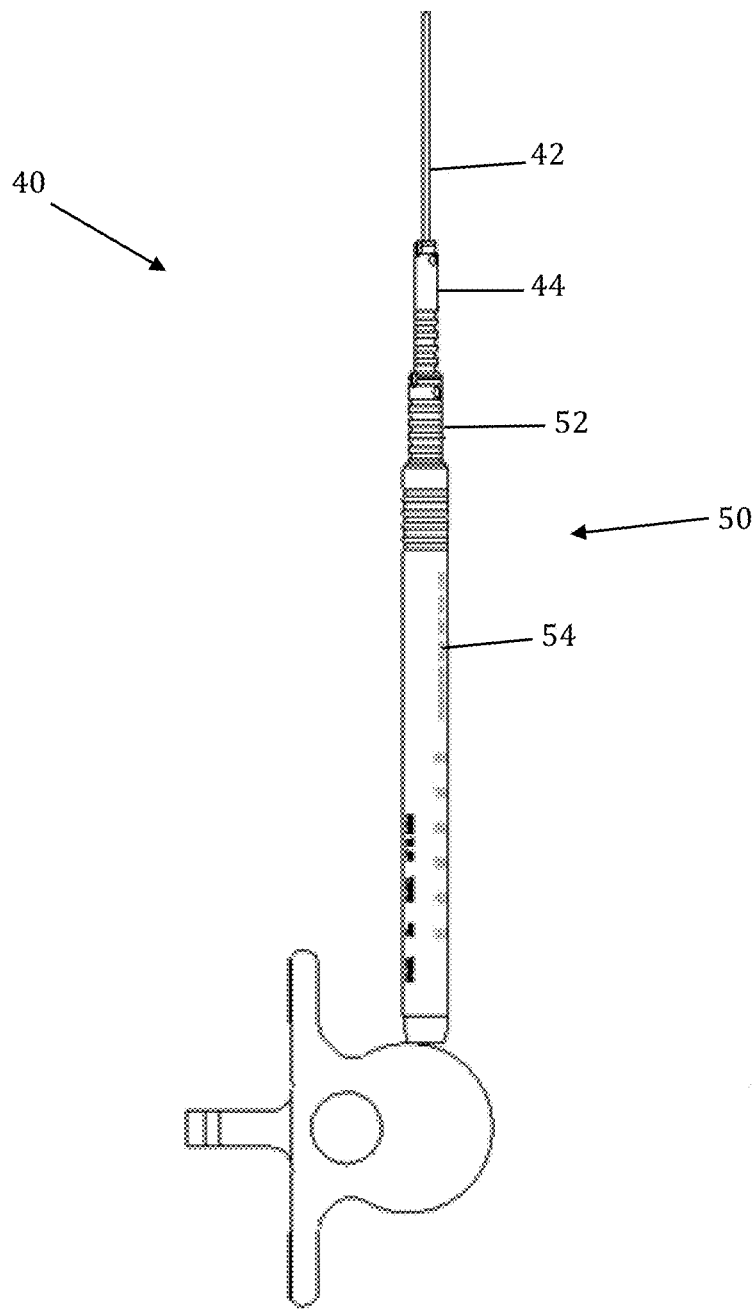
FIG. 7 is a side plan view of a tissue distraction assembly (comprising a plurality of dilating cannulae over a K-wire) used to distract tissue between the skin of the patient and the surgical target site according to one embodiment of the present disclosure.

FIG. 7 illustrates an example of a tissue distraction system 40 according to one embodiment. The tissue distraction system 40 includes a K-wire 42 and initial dilator 44, as well as a secondary dilation assembly 50. The secondary dilation assembly 50 includes at least two nesting cannulae 52, 54.

Figure 13:
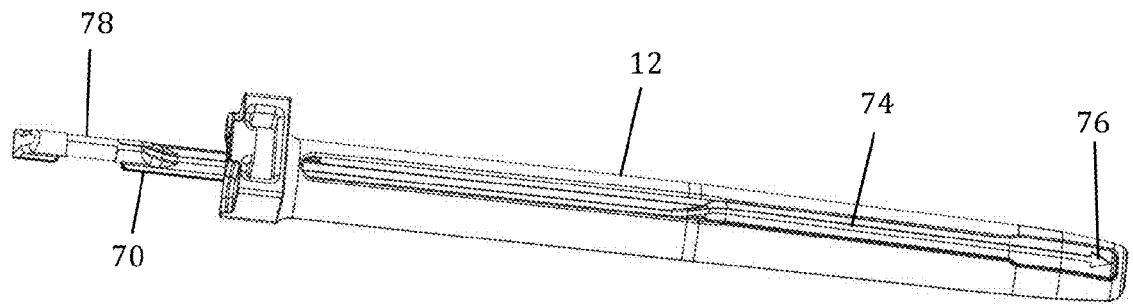
FIGS. 13-14 are perspective views of an assembly comprising the disposable electrode of FIG. 8 coupled to the retractor blade of FIG. 10.
Figure 14:
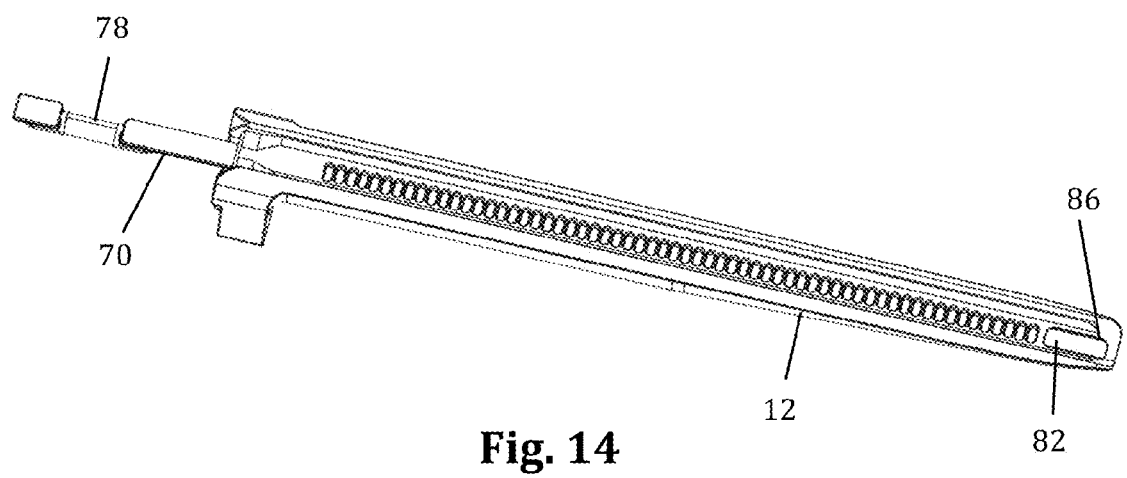
Figure 15:
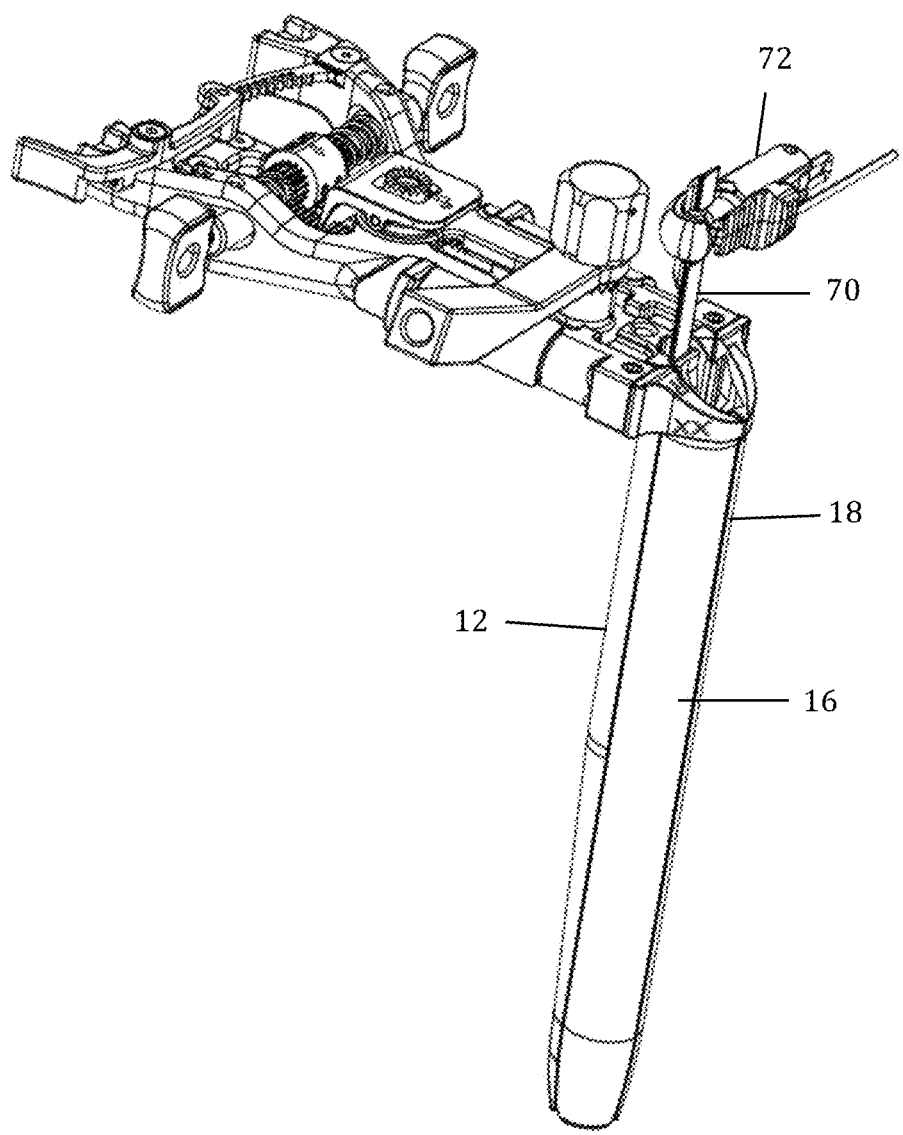
FIGS. 15-16 are perspective views of the tissue retraction assembly of FIG. 1 including the disposable electrode/blade assembly of FIG. 13.

FIGS. 8-16 illustrate an example of one embodiment of a removably couplable disposable electrode 70 and retractor blade 12 for use with the tissue retraction assembly 10 according to the present disclosure. The electrode 70 assists in the detection of the depth of nerves relative to the length of the posterior blade after the tissue retraction assembly is placed. The electrode 70 also assists in assessing the health and status of the nerves closest to the posterior blade 12 after the tissue retractor 10 is fully retracted in the open position and throughout the surgical procedure. (Open position refers to the level of retraction utilized to maintain the operative corridor to the spine during surgery.) Using a disposable electrode 70 permits the retractor blade 12 to be sterilized and reused endlessly without the possibility of degradation to the electrode. This in turn ensures that results from nerve monitoring using the electrode are consistent and reduces potentially high costs of replacing the entire blade structure if the electrode (or insulating regions surrounding the electrode) degrade. Although FIG. 15 illustrates the electrode 70 in use with only the posterior retractor blade 12, the electrode 70 could be used with each of the retractor blades 12, 16, and/or 18 without departing from the scope of this disclosure.

Figure 8:
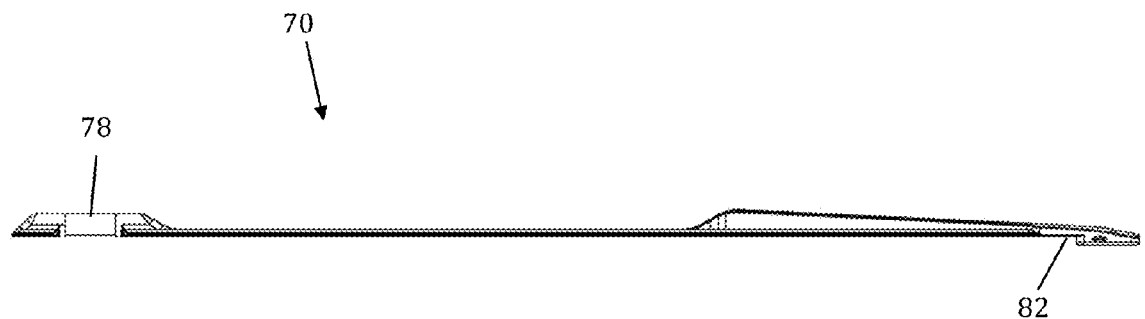
FIGS. 8-9 are side and perspective views, respectively, of an example of a disposable electrode forming part of the tissue retraction system of FIG. 1 according to one embodiment of the present disclosure.
Figure 9:
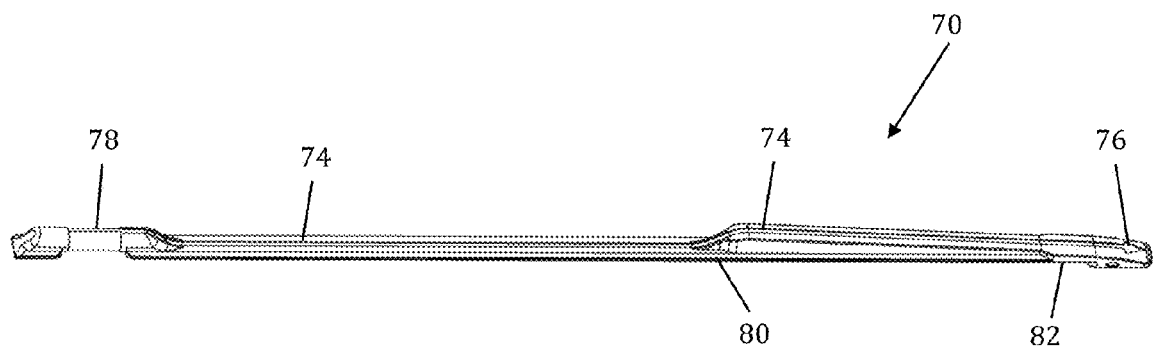
Figure 10:
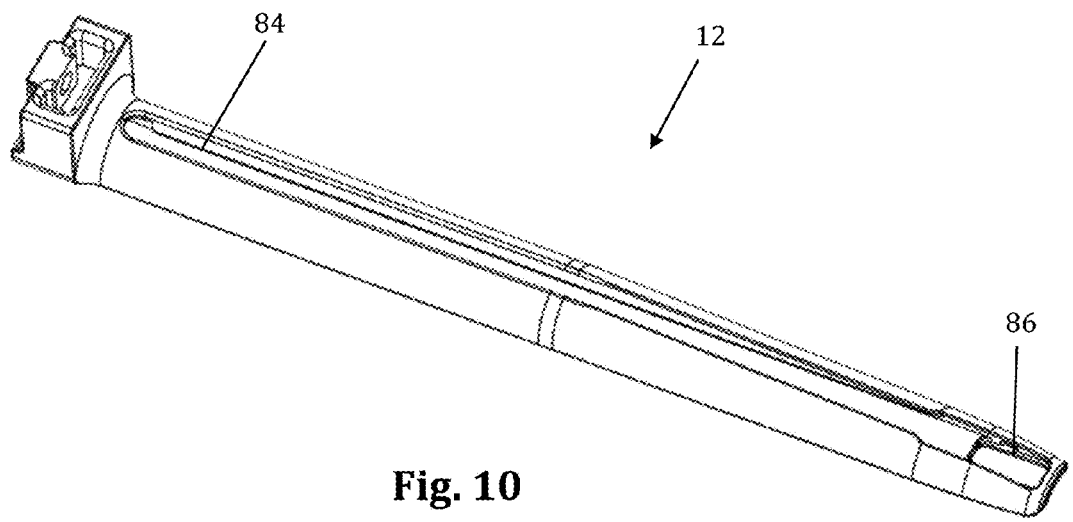
FIGS. 10-11 are perspective views of an example of a retractor blade forming part of the tissue retraction system of FIG. 1 configured to releasably couple with the disposable electrode of FIG. 9.

FIGS. 8-9 illustrate one example of an electrode 70 that includes a molded plastic part with a conductive trace 74 deposited generally along the length of the electrode 70. The conductive trace 74 may include a discrete trace for each electrode contact 76 on the electrode body 70. Preferably, the electrode 70 is made out of a generally stiff material that can also withstand bending without breaking, such as, for example, PVC. The conductive trace 74 provides a conductive pathway for the delivery of current from a current delivery source (such as a clip cable 72) to each electrode as well as for the delivery of electrical activity from nerve tissue at or near the surgical site to the neuromonitoring system. There are at least two areas along the electrode body 70 where the conductive trace 74 is exposed for enabling the delivery of current to and from the electrode 70. The proximal end of the electrode 70 has a first exposed area 78 that may wrap around the circumference of the proximal end of the electrode 70 to ensure a conductive path between the electrode 70 and a current delivery device or a current recording device (such as, for example, a clip cable 72). The first exposed area 78 can act as a stimulation conduit and allow a current delivery source to deliver an electric current to the conductive trace 74 and as a recording conduit that transmits changes in electrical current from the conductive trace 74 to the control unit 172 of the neuromonitoring system. The distal end of the electrode 70 has at least one electrode contact 76 (shown by way of example as a triangular patch) within the conductive trace 74 that can act as a stimulation conduit and allow the emitting of current to nearby tissue and as a recording conduit for recording changes in electrical current from nearby tissue. Both functions of the first exposed area 78 and distal electrode contact 76 will be explained in greater detail below. Other than the exposed areas 76, 78, the remainder of the conductive trace 74 is insulated with a dielectric coating to prevent current shunting. Any number of conductive materials suitable for completing the current pathway, such as, for example, silver, or copper may be used in the conductive trace 74 without departing from the scope of this disclosure.

Figure 16:
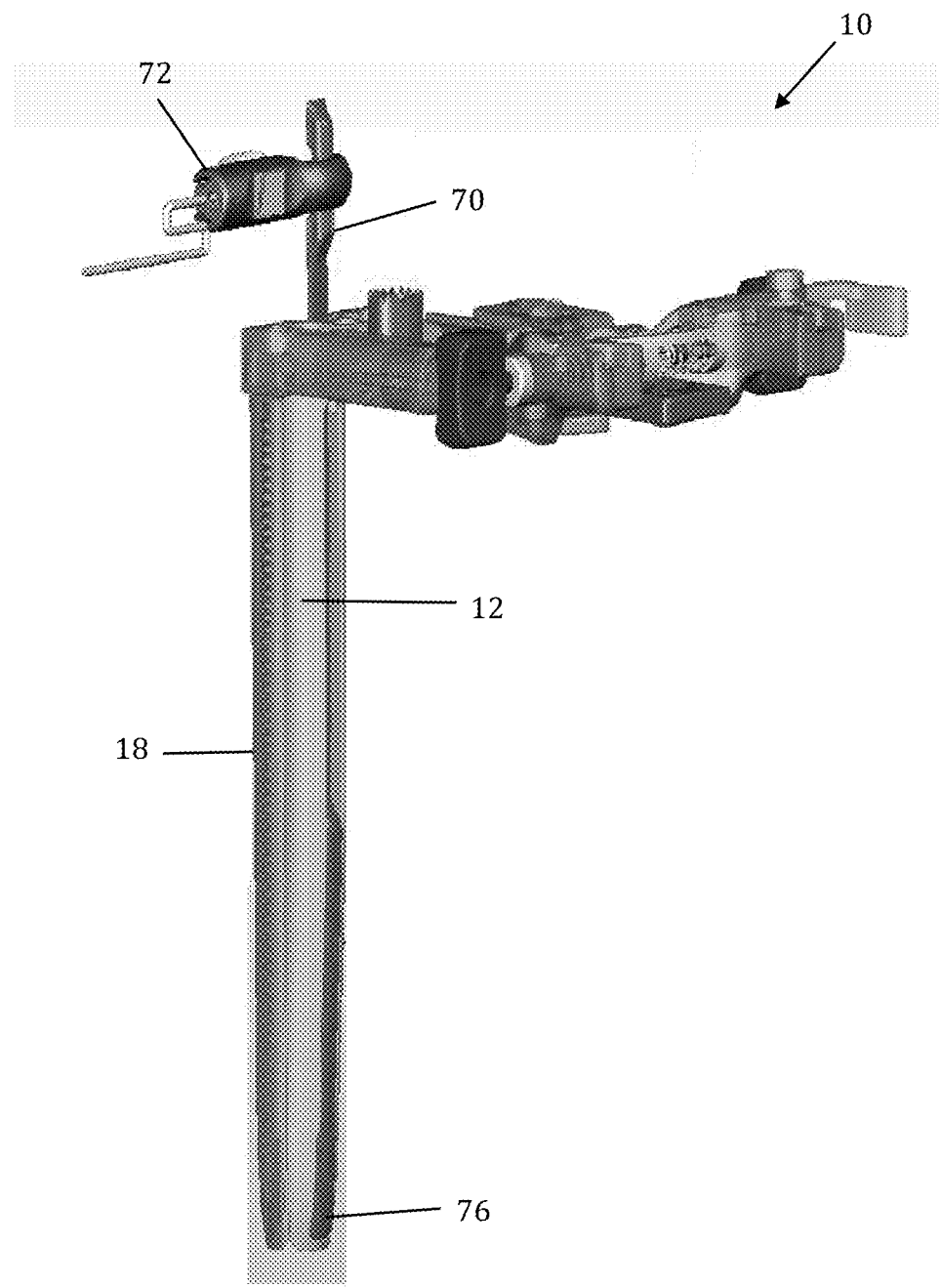

The first exposed area 78 of the disposable electrode may have a generally cylindrical shape for facilitating the connection between the electrode and a neuromonitoring system. For example, as shown in FIGS. 15-16, an electrical coupler is shown in the form of a plunger-style clip cable 72. Although shown as cylindrical, the connection site for a current delivery device or a current recording device (such as the clip cable 72) may be any size and shape necessary for making a quality electrical connection without departing from the scope of the current disclosure. The remainder of the body of the electrode 70 may be generally flat with minimal thickness and a variety of features for engaging and securing the electrode 70 to a retractor blade 12. For example, wings 80 may extend from the sides of the electrode 70 for engaging positioning features within the retractor blade 12, as will be discussed in more detail below. Additionally, the distal end of the electrode 70 may have a ledge 82 for engaging a feature of the retractor blade 12 for further secure positioning of the electrode 70 relative to the retractor blade 12, as will also be discussed in more detail below. A single sized electrode 70 may be designed for use with a variety of retractor blade 12 sizes and shapes (for example, retractor blade lengths generally ranging from 20 to 180 mm), but the electrodes may also be available in a variety of shapes and sizes.

FIGS. 13-14 illustrate one example assembly of an electrode 70 releasably coupled to retractor blade 12. Preferably, at least the posterior blade 12 is configured to enable the coupling of an electrode body 70. During assembly of the electrode body 70 to the retractor blade 12, the proximal end of the electrode 70 (more specifically, adjacent the first exposed area 78 end of the electrode 70) is inserted into generally the distal end of the retractor blade 12. The wings 80 of the electrode 70 mate with and are constrained by the dovetail grooves 84 which extend longitudinally from the distal end to the proximal end of the retractor blade 12. The dovetail grooves 84 provide an insertion guide for the disposable electrode 70 as it is inserted and assists in maintaining proper positioning of the electrode 70 while coupled to the retractor blade 12. Additionally, the ledge 82 near the distal end of the disposable electrode 70 may engage the cut-out 86 generally near the distal end of the retractor blade 12 to further assist in securing the positioning of the electrode 70 relative to the retractor blade 12. Therefore, the electrode 70 is adapted to the retractor blade 12 so that the electrode contact 76 (shown by way of example as triangular in FIGS. 9 and 13) is exposed generally along the outer surface of the blade (best shown in FIG. 13). Furthermore, the proximal end of the electrode body 70 protrudes from a machined cavity 88 (best shown in FIG. 12) at the proximal end of the retractor blade 12. Depending on the height of the blade, the proximal end may be bent or folded so as not to obstruct the surgical corridor.

Figure 17:
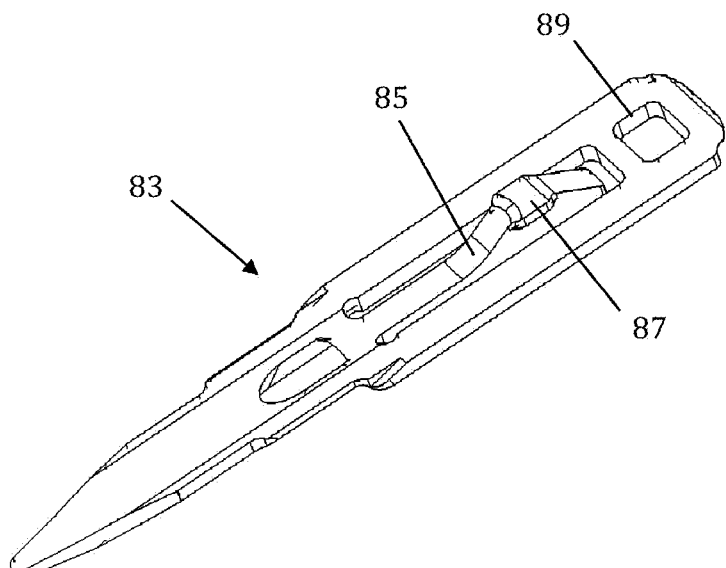
FIGS. 17-18 are perspective views of an example of an insulated locking shim for use with the posterior blade forming part of the tissue retraction system of FIG. 1 to prevent current shunting from the posterior blade when neurophysiologic monitoring is performed from the posterior blade.

FIG. 17 is illustrates a locking intradiscal shim 83 according to a second example embodiment. The locking intradiscal shim 83 is similar to the shim 56 of FIGS. 4-6 such that a description of all the like elements will not be repeated here. The locking intradiscal shim 83 of FIG. 17 is preferably coated with an insulative parylene coating to mitigate current shunting and changes to current density at the distal tip of the disposable electrode. Parylene is the trade name for a variety of chemical vapor deposited poly (p-xylylene) polymers used as moisture barriers and electrical insulators. Among such polymers, Parylene C is highly desirable due to its combination of barrier properties and manufacturing advantages. The locking intradiscal shim 83 includes a deflectable tab 85 with a lip member 87 that serves as a locking feature. The shim 83 further includes a cut-out 89 that receives an engagement tab of a removal tool.

Figure 18:
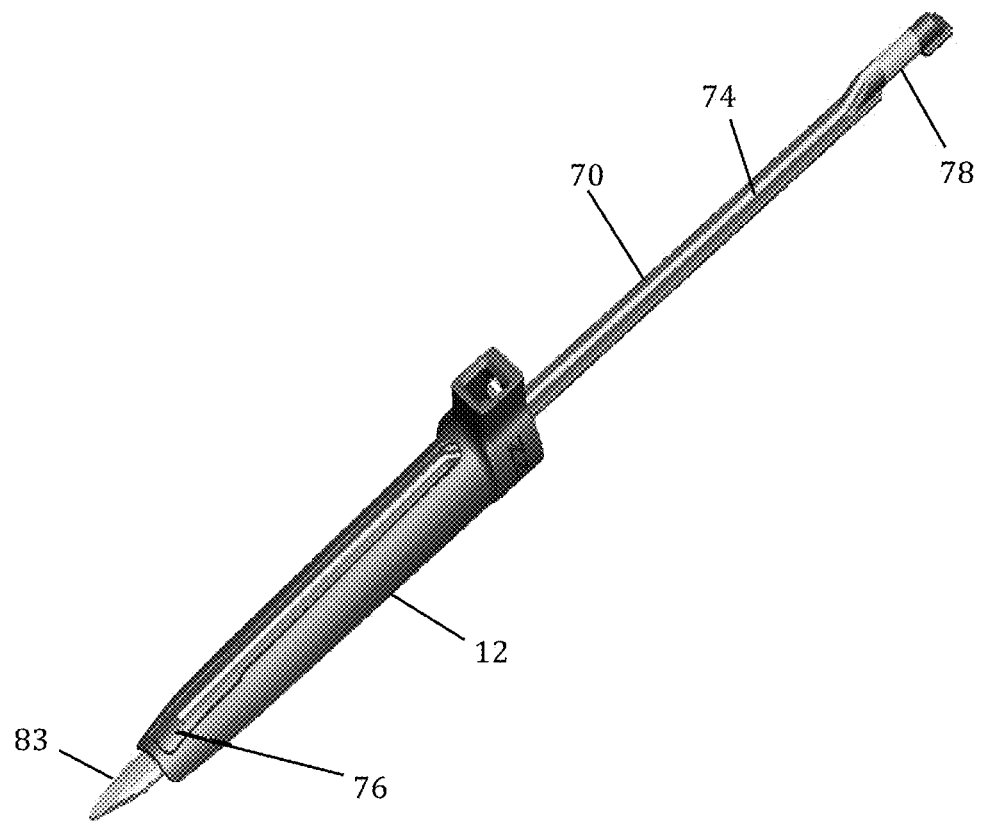

Any combination of the features described herein may be employed at any one time without departing from the scope of the present disclosure. For example, FIG. 18 illustrates the locking intradiscal shim 83 of FIG. 17 attached adjacent to the distal end of the disposable electrode 70 that is removably coupled to the posterior blade 12 described in relation to FIGS. 9-16 above. By coupling these several features, each of which include parylene coating to control shunting of electric current, better results can be achieved.

Figure 19:
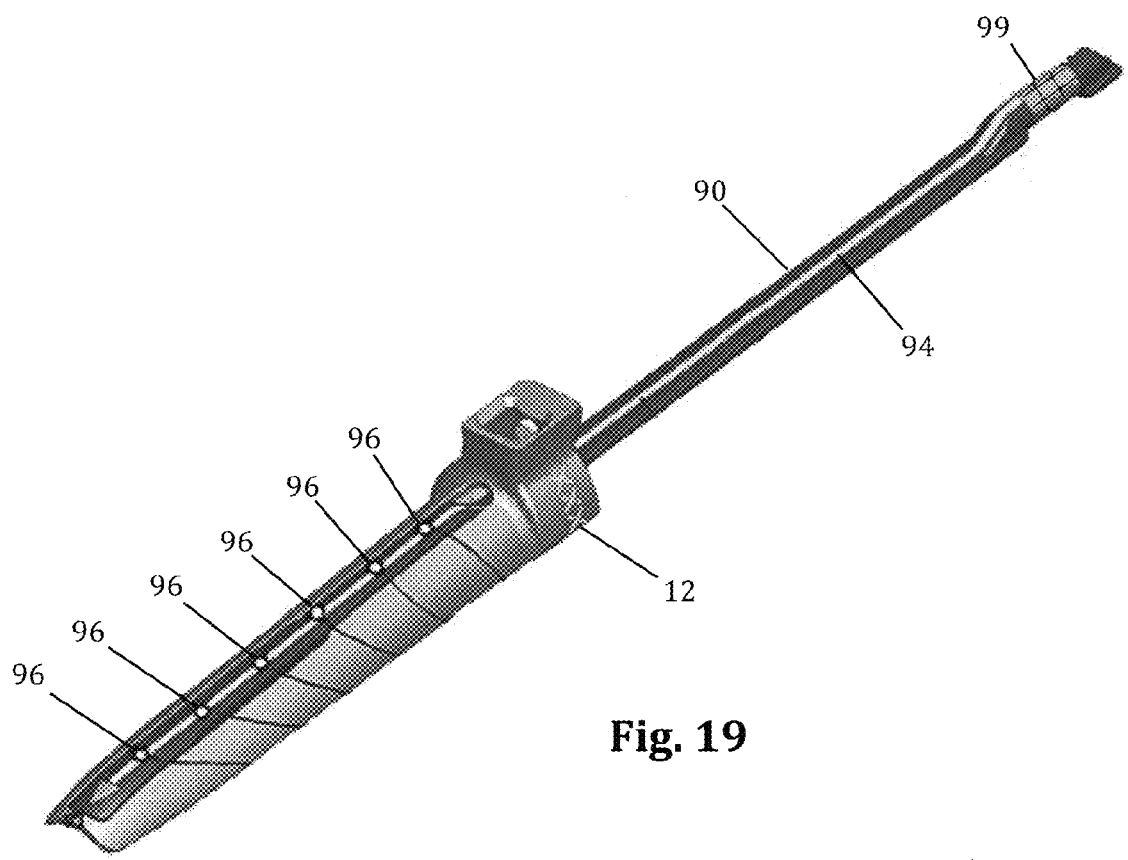
FIGS. 19-20 are perspective views of an alternative example of an electrode body with multiple electrode contacts at the distal end removeably coupled to a retractor blade, forming part of the tissue retraction system of FIG. 1.
Figure 20:
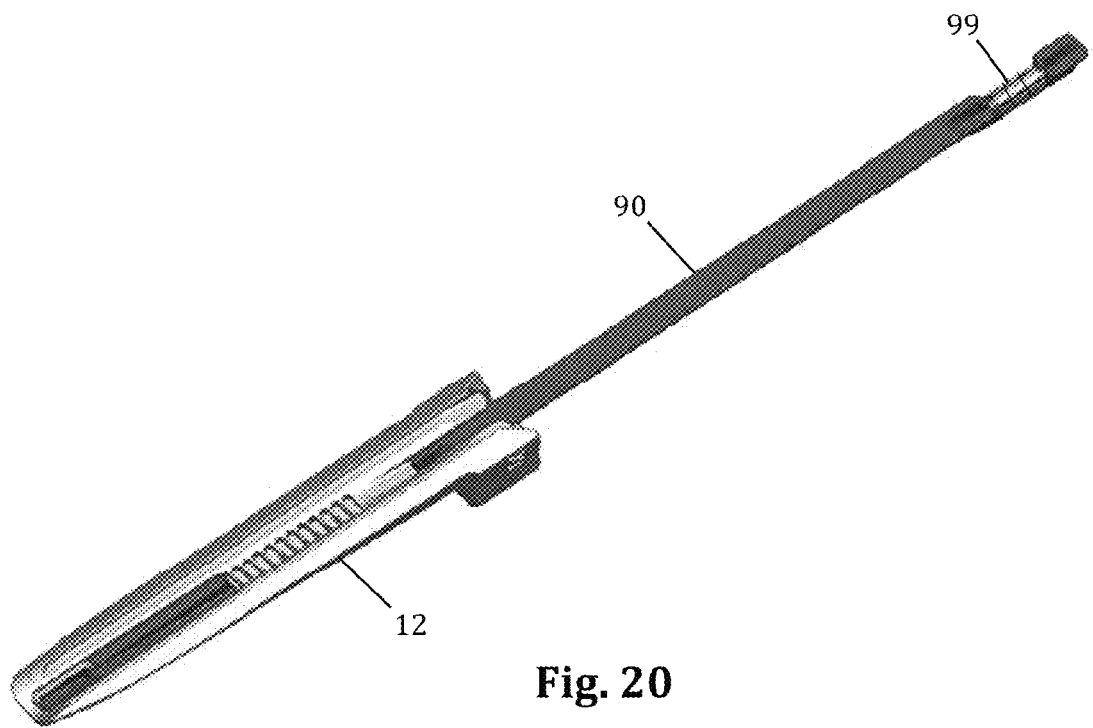

FIGS. 19-20 illustrate an alternative example of a removably couplable electrode body 90 and retractor blade 12 for use with the tissue retraction assembly 10. The electrode body 90 is similar in form to electrode body 70 described above with reference to FIGS. 8-16. The electrode body 90 of the present embodiment includes a molded plastic part with a conductive trace 94 deposited generally along the length of the electrode 90. The conductive trace 94 includes a discrete trace for each electrode contact 96 on the electrode body 90. Preferably, the electrode 90 is made out of a generally stiff material that can also withstand bending without breaking, such as, for example, PVC. The conductive trace 94 provides a conductive pathway for the delivery of current from a current delivery source to each electrode as well as for the delivery of electrical activity from nerve tissue at or near the surgical site to the neuromonitoring system. The proximal end of the electrode 90 has a multi-contact pad 99 that mates with a complimentary multi-contact coupler (not show) to provide a conductive path between the electrode 90 and a current delivery device or a current recording device (such as, for example, a clip cable 72). The multi-contact pad 99 can act as a stimulation conduit and allow a current delivery source to deliver an electric current to each discrete trace of the conductive trace 94 and as a recording conduit that transmits changes in electrical current from each electrode region 96 along the associated discrete trace of the conductive trace 94 to the control unit 172 of the neuromonitoring system. The distal end of the electrode body 90 has multiple electrode contacts 96 positioned along the length of the conductive trace 94, each one associated with a discrete trace of the conductive trace 94 that act as a stimulation conduits to allow the emitting of current to nearby tissue and as recording conduits for recording changes in electrical current from nearby tissue. FIG. 19 depicts six circular electrode contacts 96 in the conductive trace 94 spaced equidistantly along the length of the portion of the electrode body 90 that engages within the retractor blade 12. However, any number of electrode contacts 96 may be placed at any interval along any length of the engaged portion of the electrode body 90. The electrode body 90 is adapted to the retractor blade 12 so that the electrode contacts 96 are exposed generally along the outer surface of the blade 12. Other than the exposed areas 96, 99, the remainder of the conductive trace 94 is insulated with a dielectric coating to prevent current shunting. Any number of conductive materials suitable for completing the current pathway, such as, for example, silver, or copper may be used in the conductive trace 94 without departing from the scope of this disclosure. All other features of the electrode body 90, including but not limited to engagement with the retractor blade 12, are identical in form and function to the features described in relation to electrode body 70.

Figure 21:
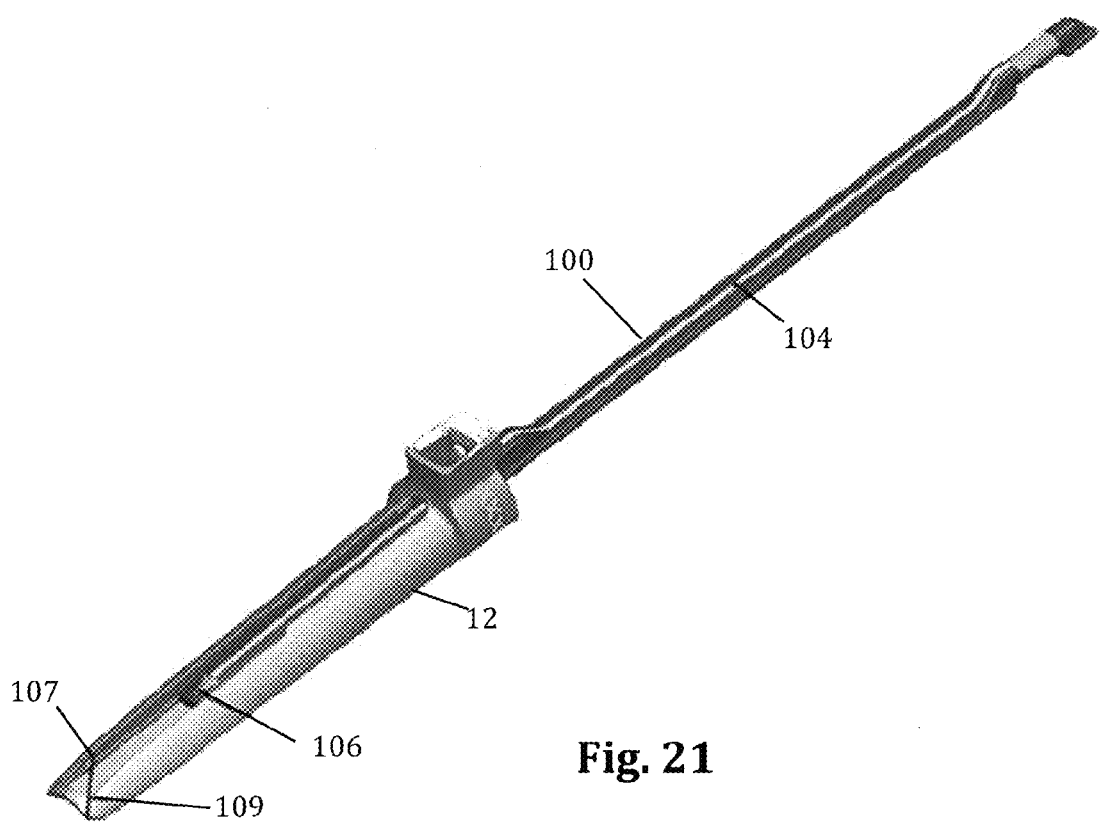
FIGS. 21-24 are perspective views of another alternative example of an electrode body with a single electrode at the distal end that is moveable within, and removeably couplable to, a retractor blade, forming part of the tissue retraction system of FIG. 1.
Figure 22:
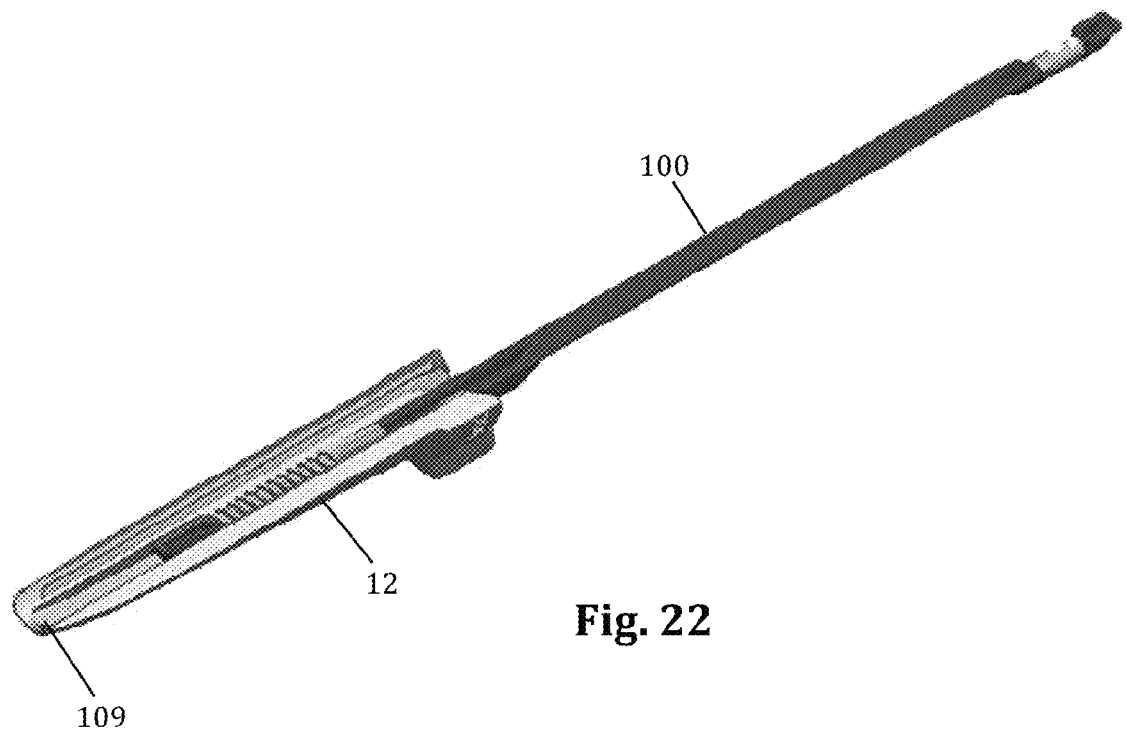
Figure 23:
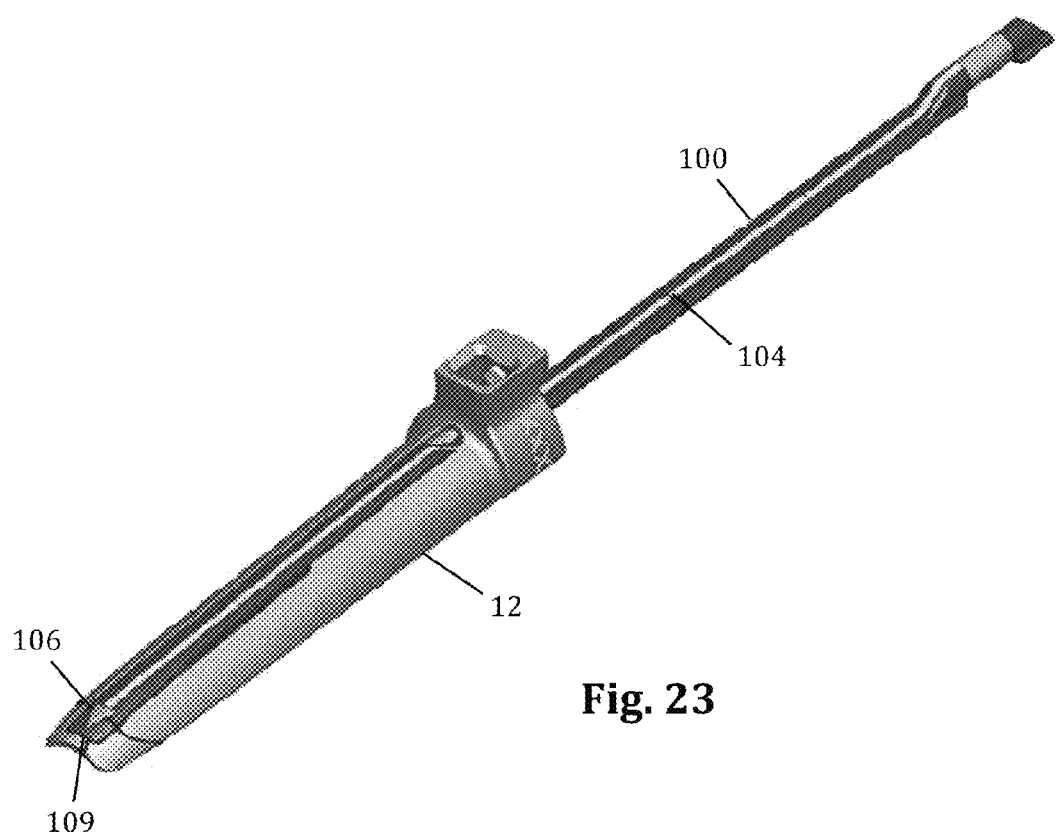
Figure 24:
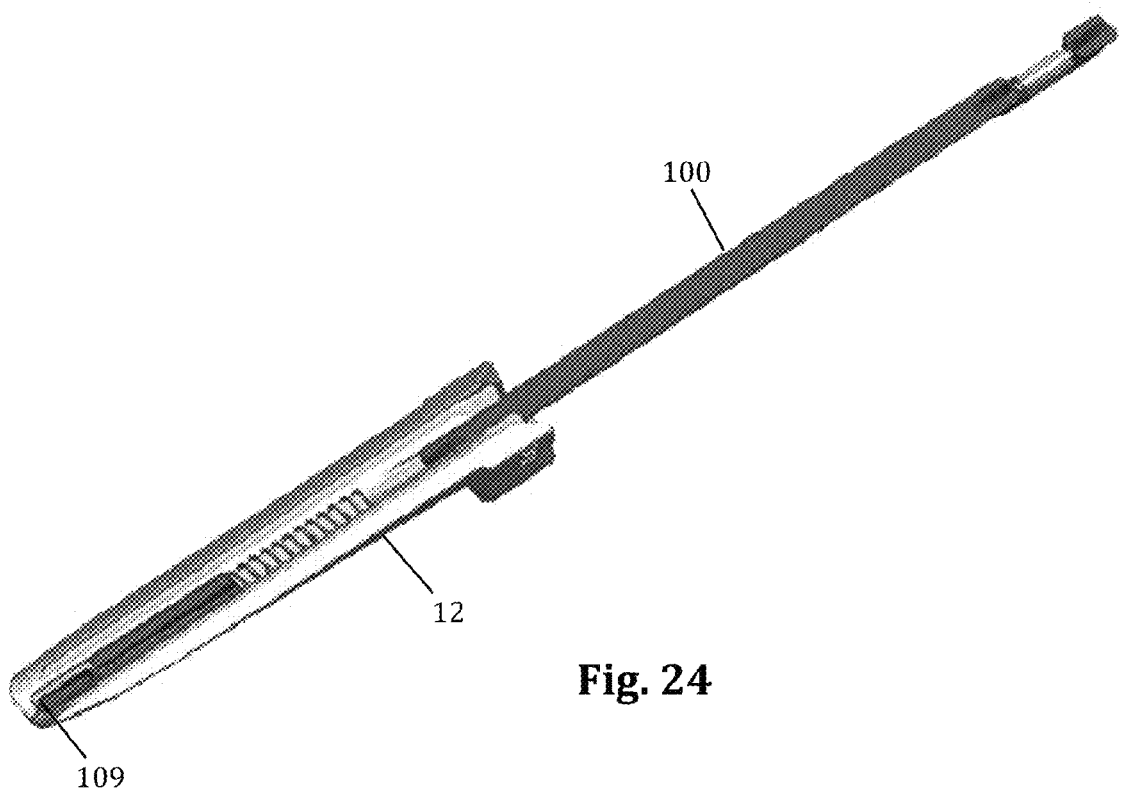

FIGS. 21-24 illustrate an example of another embodiment of an electrode body 100 and retractor blade 12 for use with the tissue retraction assembly. The electrode body 100 of this embodiment shares many features as the electrode body 90 of FIGS. 19-20 such that common features will not be repeated. However, in this embodiment, it is noted that there is only one electrode contact 106 at the distal end of the conductive trace 104. Furthermore, there is no ledge at the distal end for secured positioning relative to the distal end of the retractor blade 12. The dovetailed grooves 107 of the retractor blade 12 are preferably sized and dimensioned so that the wings on the sides of the electrode body 100 may slide smoothly along the length of the retractor blade 12 via the dovetailed grooves 107. According to some implementations, the electrode body 100 may be moveable within the retractor blade 12 such that an ideal positioning for the electrode body 100 may be found at one of several locations along the length of the retractor blade 12. Once this optimal position is found, it may be kept in place by one or more securing features. By way of example only, the proximal end may be bent or folded. Alternatively, the proximal end may be locked into position using a locking means (including but not limited to a cam lock, clamp, ramp, push-button, and spring-loaded button). Also, there may be a series of indentations along the inside of the dovetailed grooves 107 that correspond to protrusions on the wings such that the electrode body advances through a series of discrete positions within the dovetailed grooves 107 and stops at the desired location. Also, the distal end of the retractor blade 12 may include one or more advancement restriction features 109 that prevent the electrode body 100 from extending past the distal tip of the retractor blade 12. By way of example only, FIGS. 21-22 illustrate the electrode body 100 coupled with the retractor blade 12 in the proximal-most position (e.g. no advancement), and FIGS. 23-24 illustrate the electrode body 100 coupled with the retractor blade 12 in the distal-most position (e.g. maximum advancement).

Figure 25:
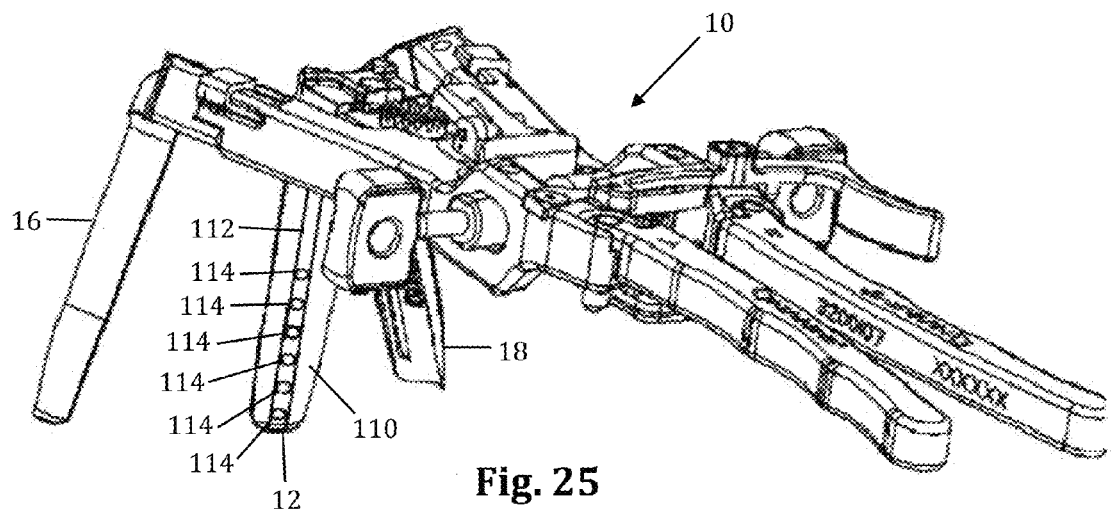
FIG. 25 is a perspective view of an example of a retractor blade having multiple electrode contacts at the distal end, forming part of the tissue retraction system of FIG. 1.

FIG. 25 illustrates another exemplary embodiment. The retractor blade 12 and electrode area of this embodiment shares many features as the electrode body of FIGS. 19-20 such that common features will not be repeated. However, in this embodiment, the posterior face 110 of the posterior blade 12 includes a conductive trace 112 extending longitudinally therealong. The conductive trace 112 provides a conductive pathway for the delivery of current from a current delivery source to the retractor blade 12 itself as well as for the delivery of electrical activity from nerve tissue at or near the surgical site to the neuromonitoring device. The posterior face 110 of the retractor blade 12 has at least one electrode contact 114 within the conductive trace 110 and this at least one electrode contact 114 can act as a stimulation conduit and allow a current for the emitting or receiving of electric current from the posterior face 110 of the retractor blade 12. Other than the electrode contact(s) 114, the remainder of the conductive trace 110 is insulated with a dielectric coating to prevent current shunting. Any number of conductive materials suitable for completing the current pathway, such as, for example, silver, or copper may be used in the conductive trace 110 without departing from the scope of this disclosure. According to the implementation show in FIG. 25, there is provided one conductive trace 110 along the longitudinal axis of the retractor blade 12 that includes 6 discrete traces, each one ending in one of six electrode contacts 114 that serve as stimulation conduits (for recording or stimulating purposes as set forth above). At the proximal end of the retractor blade the conductive trace 110 may end with a multi-contact pad (not shown) that is mateable with a suitable multi-contact coupler. Any number of suitable couplers would be readily apparent to a person of skill in the art. For example, the pad may be situated on a post that is received within a female socket coupler. It is to be appreciated that while six electrode contact regions are shown, the blade 12 could include more or less than six electrodes regions.

Figure 26:
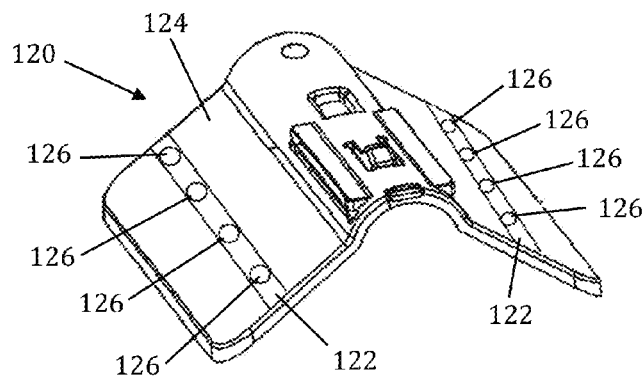
FIG. 26 is a perspective view of an example of a posterior shim element having multiple electrode contacts, the posterior shim element couplable to a retractor blade forming part of the tissue distraction system of FIG. 1.
Figure 27:
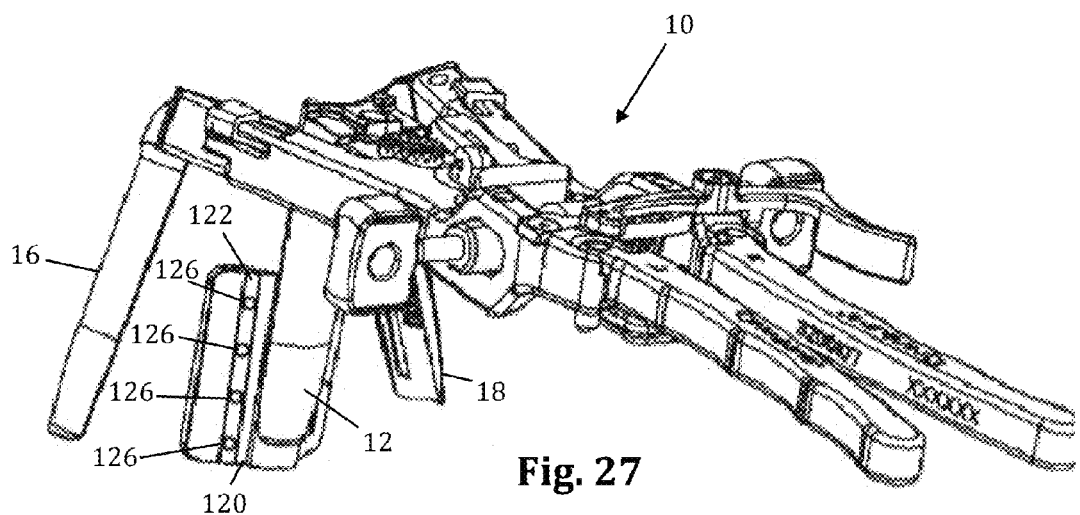
FIG. 27 is a perspective view of the posterior shim element of FIG. 26 coupled with a retractor blade forming part of the tissue distraction system of FIG. 1.

FIGS. 26-27 illustrate another exemplary embodiment in which the retractor blade 12 is further equipped with a posterior shim element 120. The posterior shim element 120 may include a molded plastic part with at least one conductive trace 122 disposed on its posterior face 124. Preferably, the posterior shim element 120 is made out of a generally stiff material that can also withstand bending without breaking, such as, for example, PVC. The conductive trace 122 provides a conductive pathway for the delivery of current from a current delivery source (such as a clip cable 72 attached to the shim itself, the retractor blade, and/or the disposable electrode) to the posterior face 124 of the posterior shim element 120 as well as for the delivery of electrical activity from nerve tissue at or near the surgical site to the neuromonitoring device. The posterior face 124 of the posterior shim element 120 has at least one electrode contact 126 within each conductive trace 122 and this at least one electrode contact 126 can act as a stimulation conduit and allow a current for the emitting or receiving of electric current from the posterior face 124 of the posterior shim element 120. Other than the electrode contact(s) 126, the remainder of the conductive trace 122 is insulated with a dielectric coating to prevent current shunting. Each conductive trace will include a discrete trace for each electrode contact 126 associated with the trace. Any number of conductive materials suitable for completing the current pathway, such as, for example, silver, or copper may be used in the conductive trace without departing from the scope of this disclosure. According to the implementation show in FIGS. 26-27, the posterior shim element 120 includes two conductive trace elements 122, with one conductive trace 122 positioned on either side of the longitudinal axis of the retractor blade 12. To couple the shim to the stimulation source, each trace may include, for example, a wire extension with multi-contact pad that may extend out of the operating corridor when the shim is positioned. Along each conductive trace 122, there are four electrode contacts 126 that serve as stimulation conduits (for recording or stimulating purposes as set forth above), and thus each trace 122 includes four discrete traces. It is to be appreciated that while four electrode contact regions are shown for each trace 122, the more or less than for electrode contacts may be included along each trace 122.

Figure 28:
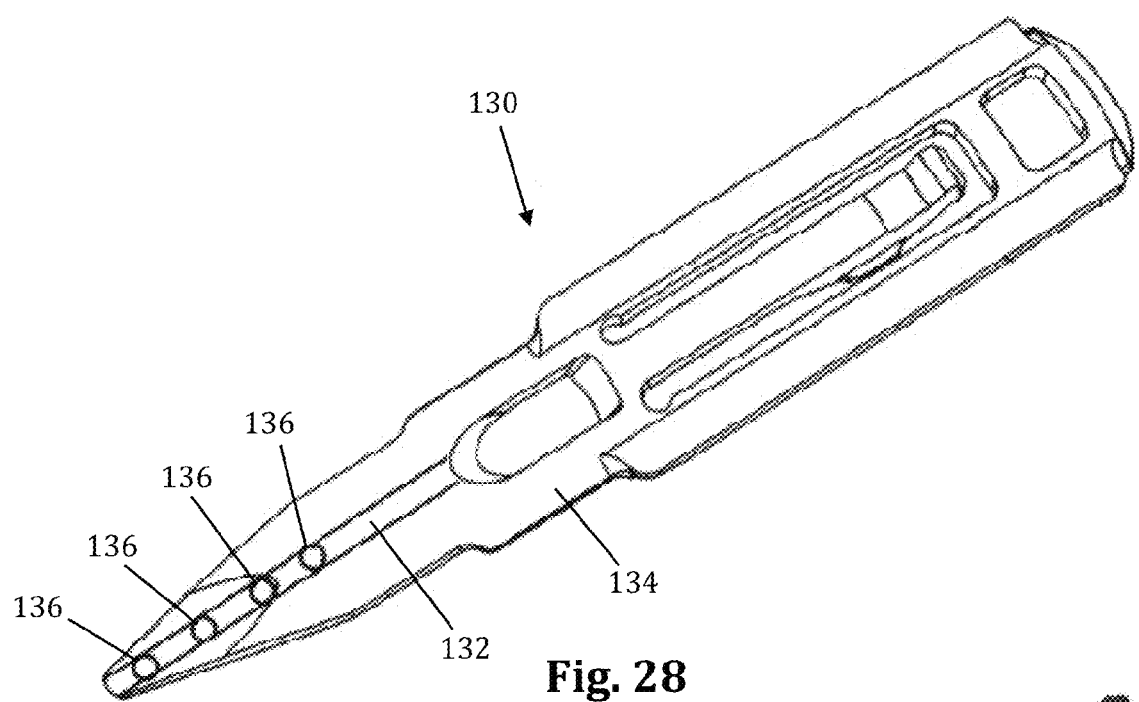
FIGS. 28-29 are perspective views of one example of a locking intradiscal shim having electrode contacts are the distal end and coupled to a retractor blade forming part of the tissue retraction system of FIG. 1.
Figure 29:
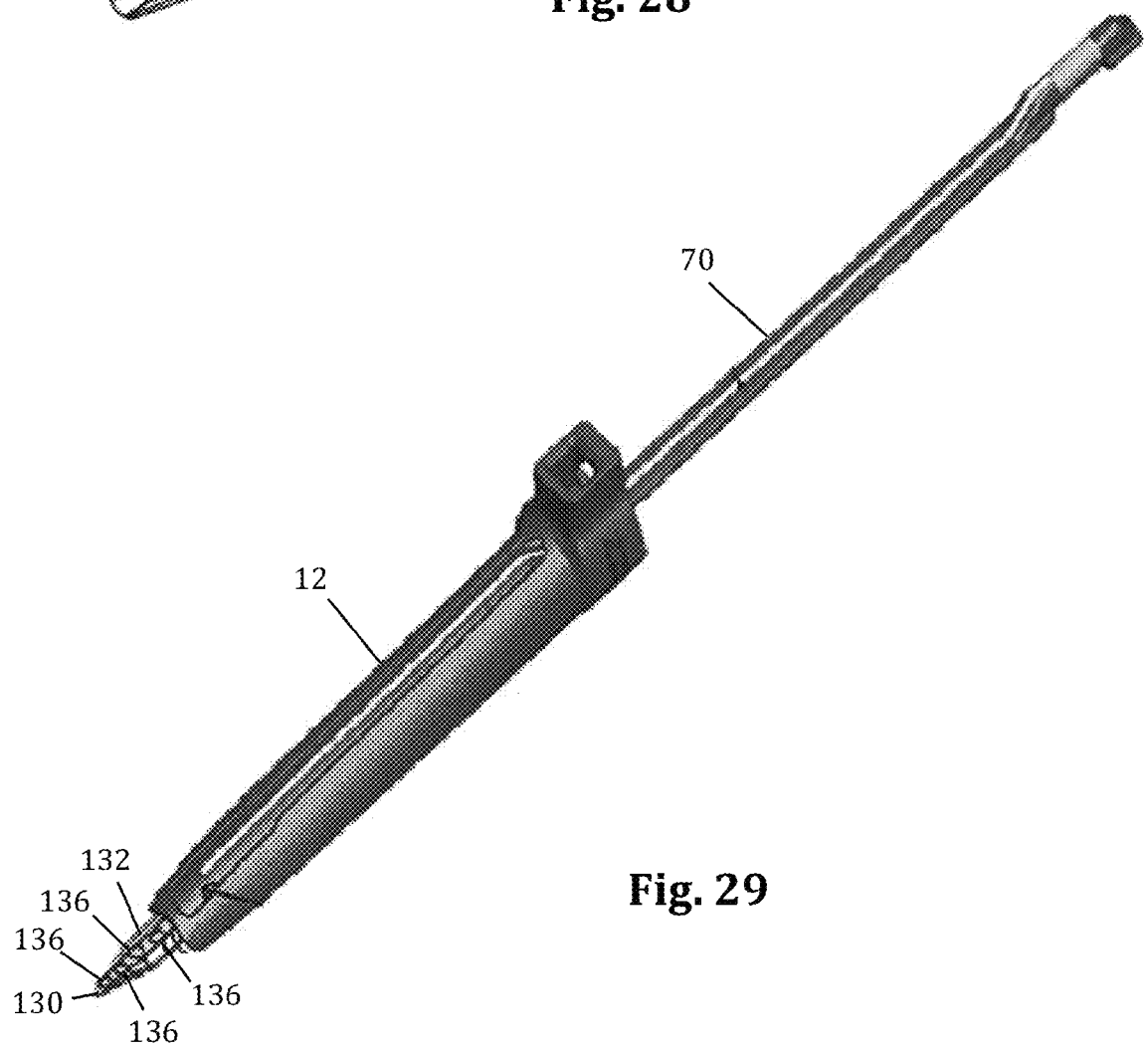

According to another embodiment shown in FIGS. 28-29, the posterior shim element may be a locking intradiscal shim 130 removably couplable to the retractor blade 12. The locking intradiscal shim 130 of the current embodiment is substantially similar in structure to the locking intradiscal shim 56 described above with reference to FIGS. 4-6 such that common features need not be repeated. The locking intradiscal shim 130 may include a molded plastic part with a conductive trace 132 deposited on its posterior face 134. Preferably, the posterior shim element 130 is made out of a generally stiff material that can also withstand bending without breaking, such as, for example, PVC. The conductive trace 132 provides a conductive pathway for the delivery of current from a current delivery source (such as a clip cable 72 attached to the shim itself, the retractor blade, and/or the disposable electrode) to the posterior face 134 of the locking intradiscal shim 130 as well as for the delivery of electrical activity from nerve tissue at or near the surgical site to the neuromonitoring device. The posterior face 134 of the locking distal shim 130 has at least one electrode contact 136 within the conductive trace 134 and this at least one electrode contact 136 can act as a stimulation current and allow a current for the emitting or receiving of electric current from the posterior face 134 of the locking intradiscal shim 130. The conductive trace 134 includes a discrete trace for each of the at least one electrodes. Other than the electrode contact(s) 136, the remainder of the conductive trace 132 is insulated with a dielectric coating to prevent current shunting. Any number of conductive materials suitable for completing the current pathway, such as, for example, silver, or copper may be used in the conductive trace 132 without departing from the scope of this disclosure. According to the implementation show in FIG. 28, four electrode contacts 136 are shown and are generally disposed linearly along the length of the locking intradiscal shim 130. These electrode contacts 136 can serve as a stimulation conduit (acting as either a stimulation site or a recording site as set forth above). However, it is to be appreciated that any number of electrode contacts 136 may be provided in any number of configurations.

For the sake of illustration purposes only, the shim 120 of FIG. 26-27 is coupled to a retractor blade 12 whereas the shim 130 of FIGS. 28-29 coupled to a retractor blade-electrode body assembly. It is to be appreciated that the shims of the current disclosure may be used with either configuration.

As mentioned above, any number of distraction components and/or retraction components (including but not limited to those described herein) may be equipped to detect the presence of (and optionally the distance and/or direction to) neural structures during tissue distraction and/or retraction. This is accomplished by employing the following steps: (1) one or more stimulation electrodes are provided on the various distraction and/or retraction components; (2) a stimulation source (e.g. voltage or current) is coupled to the stimulation electrodes; (3) a stimulation signal is emitted from the stimulation electrodes as the various components are advanced towards or maintained at or near the surgical target site; and (4) the patient is monitored to determine if the stimulation signal causes muscles associated with nerves or neural structures within the tissue to innervate. If the nerves innervate, this may indicate that neural structures may be in close proximity to the distraction and/or retraction components.

Figure 30:
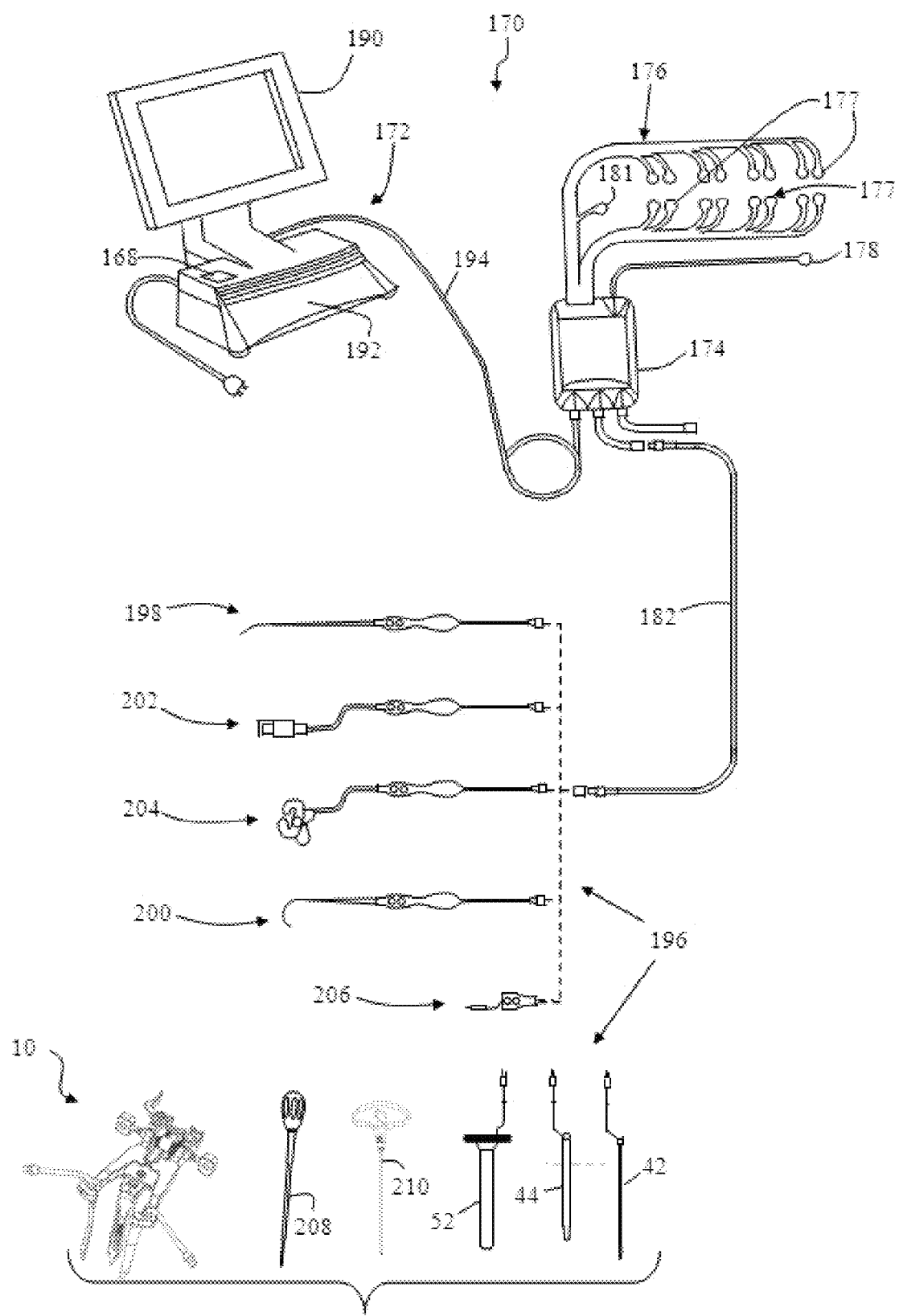
FIG. 30 is a perspective view of an example of a nerve monitoring system programmed to perform nerve monitoring before, during and after the creation of an operative corridor to a surgical target site using the surgical access system of FIG. 1 in accordance with the present disclosure.
Figure 31:
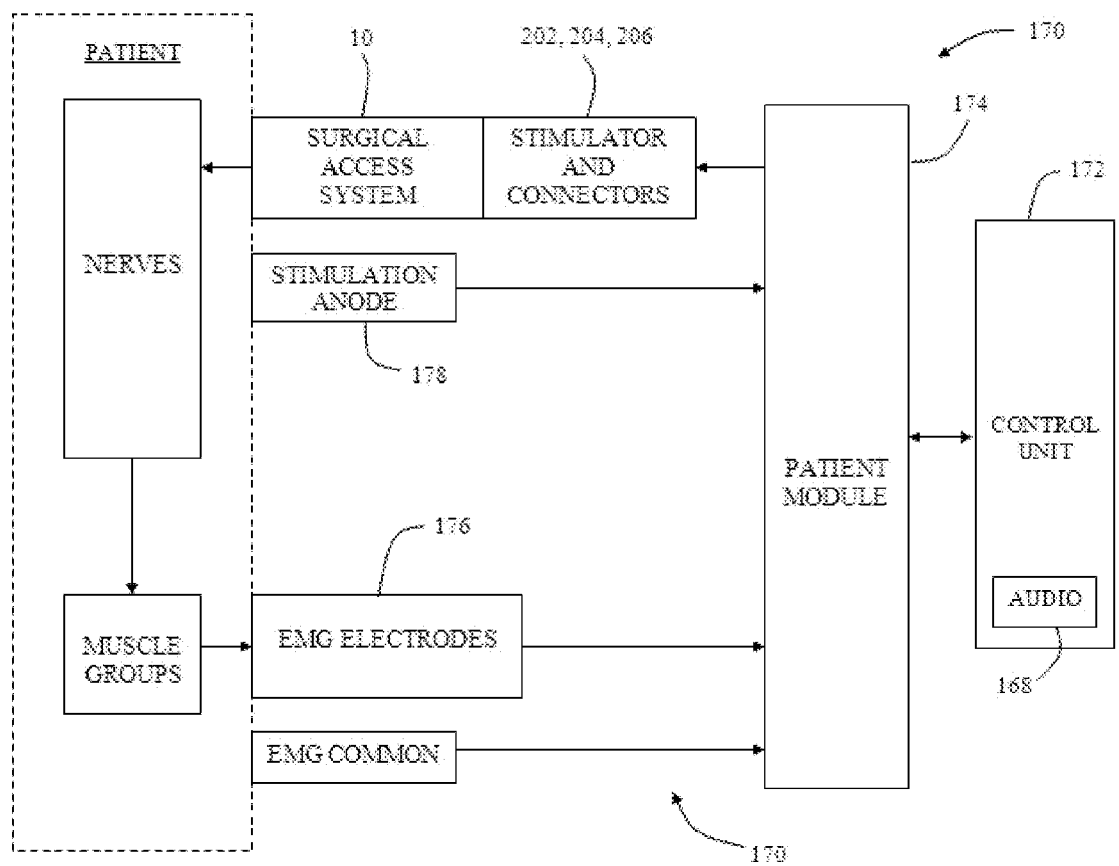
FIG. 31 is a block diagram of the nerve monitoring system shown in FIG. 30.

FIGS. 30-31 illustrate, by way of example only, a monitoring system 170 suitable for use with the surgical access system 10 of the present disclosure. The monitoring system 170 includes a control unit 172, a patient module 174, and an EMG harness 176 and return electrode 178 coupled to the patient module 174, and a cable 182 for establishing electrical communication between the patient module 174 and any number of surgical accessories 196, including the surgical access system of the present disclosure (retractor assembly 10 of FIG. 1 and distraction assemblies 40, 50 of FIG. 7, including K-wire 42, initial dilator 44 and sequentially dilating cannulae 52, 54). The surgical accessories 196 may further include, but are not necessarily limited to, devices for performing pedicle screw tests (such as a screw test probe 198), neural pathology monitoring devices (such as a nerve root retractor 200), coupling devices for electronically coupling surgical instruments to the system 170 (such as electric coupling devices 202, 204 and stimulator driver 206), and pilot hole forming components (such as a tap member 208, pedicle access probe 210, or other similar device). More specifically, this electrical communication can be achieved by providing, by way of example only, a hand-held stimulation driver 206 capable of selectively providing a stimulation signal (due to the operation of manually operated buttons on the hand-held stimulation controller 206) to one or more connectors (e.g., coupling devices 202, 204). The coupling devices 202, 204 are suitable to establish electrical communication between the hand-held stimulation controller 206 and (by way of example only) the stimulation electrodes on the K-wire 42, the dilators 44, 52, 54, the retractor blades 12, 16, 18, and/or the shim element 56 (collectively "surgical access instruments").

In order to use the monitoring system 170, then, these surgical access instruments must be connected to at least one of coupling devices 202, 204 (or similar couplers including multi-contact regions, not shown), at which point the user may selectively initiate a stimulation signal (preferably, a current signal) from the control unit 172 to a particular surgical access instruments. Stimulating the electrode(s) on these surgical access instruments before, during, and/or after establishing operative corridor will cause nerves that come into close or relative proximity to the surgical access instruments to depolarize, producing a response in a myotome associated with the innervated nerve.

The control unit 172 includes a touch screen display 190 and a base 192, which collectively contain the essential processing capabilities (software and/or hardware) for controlling the monitoring system 170. The control unit 172 may include an audio unit 168 that emits sounds according to a location of a surgical element with respect to a nerve. The patient module 174 is connected to the control unit 172 via a data cable 194, which establishes the electrical connections and communications (digital and/or analog) between the control unit 172 and patient module 174. The main functions of the control unit 172 include receiving user commands via the touch screen display 190, activating stimulation electrodes on the surgical access instruments, processing signal data according to defined algorithms, displaying received parameters and processed data, and monitoring system status and report fault conditions. The touch screen display 190 is preferably equipped with a graphical user interface (GUI) capable of communicating information to the user and receiving instructions from the user. The display 190 and/or base 192 may contain patient module interface circuitry (hardware and/or software) that commands the stimulation sources, receives digitized signals and other information from the patient module 174, processes the EMG responses to extract characteristic information for each muscle group, and displays the processed data to the operator via the display 190.

In one embodiment, the monitoring system 170 is capable of determining nerve direction relative to one or more of the K-wire 42, the dilators 44, 52, 54, the retractor blades 12, 16, 18, and/or the shim element 56 before, during and/or following the creation of an operative corridor to a surgical target site. Monitoring system 170 accomplishes this by having the control unit 172 and patient module 174 cooperate to send electrical stimulation signals to one or more of the stimulation electrodes provided on these instruments. Depending upon the location of the surgical access system 10 within a patient (and more particularly, to any neural structures), the stimulation signals may cause nerves adjacent to or in the general proximity of the surgical access system 10 to depolarize. This causes muscle groups to innervate and generate EMG responses, which can be sensed via the EMG harness 176. The nerve direction feature of the system 170 is based on assessing the evoked response of the various muscle myotomes monitored by the system 170 via the EMG harness 176.

By monitoring the myotomes associated with the nerves (via the EMG harness 176 and recording electrode 177) and assessing the resulting EMG responses (via the control unit 172), the surgical access system 10 is capable of detecting the presence of (and optionally the distant and/or direction to) such nerves. This provides the ability to actively negotiate around or past such nerves to safely and reproducibly form the operative corridor to a particular surgical target site, as well as monitor to ensure that no neural structures migrate into contact with the surgical access system 10 after the operative corridor has been established. In spinal surgery, for example, this is particularly advantageous in that the surgical access system 10 may be particularly suited for establishing an operative corridor to an intervertebral target site in a postero-lateral, trans-psoas fashion so as to avoid the bony posterior elements of the spinal column.

Figure 32:
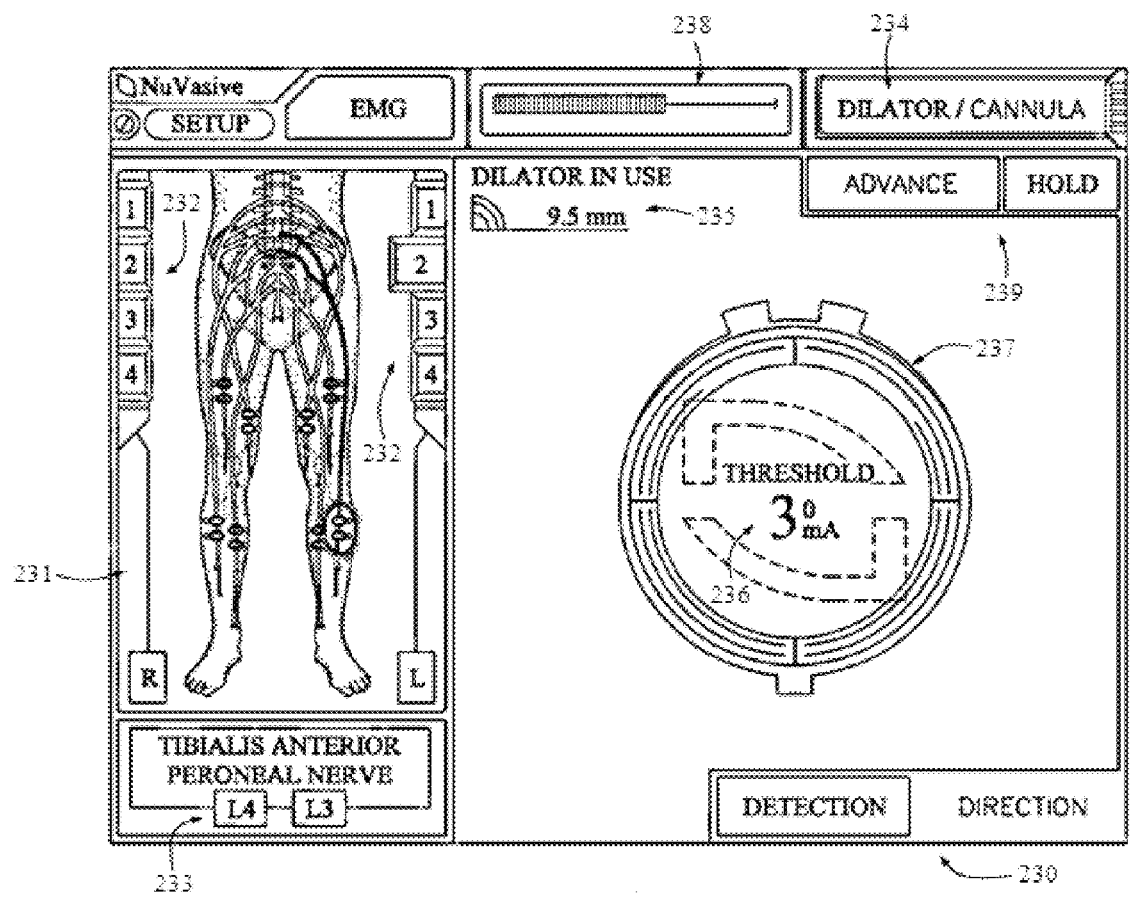
FIGS. 32-33 are examples of screen displays illustrating exemplary features and information communicated to a user during the use of the nerve monitoring system of FIG. 30.
Figure 33:
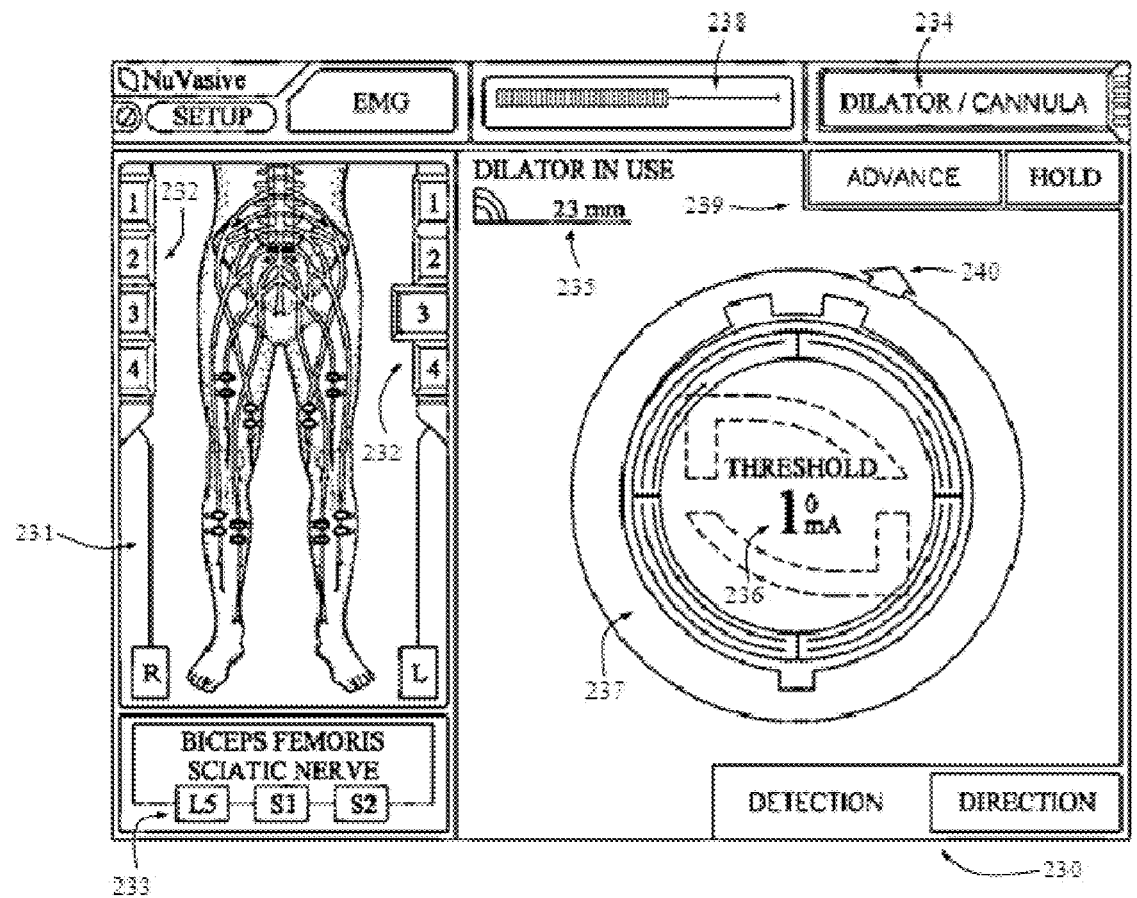

FIGS. 32-33 are exemplary screen displays (to be shown on the display 190) illustrating one embodiment of the nerve direction feature of the monitoring system shown and described with reference to FIG. 30-31. These screen displays are intended to communicate a variety of information to the surgeon in an easy-to-interpret fashion. This information may include, but is not necessarily limited to, a display of the function 230 (in this case "DIRECTION"), a graphical representation of a patient 231, the myotome levels being monitored 232, the nerve or group associated with a displayed myotome 233, the name of the instrument being used 234 (in this case, a dilator 52, 54), the size of the instrument being used 235, the stimulation threshold current 236, a graphical representation of the instrument being used 237 (in this case, a cross-sectional view of a dilator 52, 54) to provide a reference point from which to illustrate relative direction of the instrument to the nerve, the stimulation current being applied to the stimulation electrodes 238, instructions for the user 239 (in this case, "ADVANCE" and/or "HOLD"), and an arrow 240 indicating the direction from the instrument to a nerve. This information may be communicated in any number of suitable fashions, including but not limited to the use of visual indicia (such as alpha-numeric characters, light-emitting elements, and/or graphics) and audio communications (such as a speaker element). Although shown with specific reference to a dilating cannula (such as at 234), it is to be readily appreciated that the present disclosure is deemed to include providing similar information on the display 190 during the use of any or all of the various instruments forming the surgical access system 10 of the present disclosure, including the distraction assembly 40 (i.e. the K-wire 42 and dilators 44, 52, 54) and/or the retractor blades 12, 16, 18 and/or the shim element 56.

As mentioned previously, a neuromonitoring system such as the one shown and described in the above-mentioned '045 patent (incorporated by reference) may perform nerve proximity testing on one or more nerves of interest to ensure safe and reproducible access to a surgical target site and maintenance of the lateral access corridor. According to a first broad aspect of the present disclosure, the depth of a nerve of interest relative to a component of the surgical access assembly is localized, preferably prior to retraction of tissue from the lateral access corridor. According to a second broad aspect, the nerve of interest is stimulated at a location distal to the site of retraction and a response is recorded from a location proximal to the site of retraction. According to a third broad aspect, neurophysiologic responses across the site of retraction are recorded at multiple time points during a surgical procedure and are compared to previous responses. Changes in the neurophysiologic responses over time may provide useful information as to the health and status of the nerve.

One particular nerve of interest during lateral surgery to the lumbar spine is the femoral nerve. The femoral nerve descends the posterior aspect of the lateral spine at approximately the L2-4 levels and gradually moves towards the anterior aspect of the lateral spine at approximately the level of the L4-5 disc space. Therefore, the femoral nerve may come in close proximity to one or more blades of the retractor such that monitoring the depth, health, and status of the femoral nerve during retraction of tissue to maintain the lateral access corridor may be desirable. The neuromonitoring system may perform testing to ascertain femoral nerve depth and proximity, as well as the effect of retraction on the femoral nerve across the site of retraction. Such testing helps ensure safe and reproducible access to the surgical target site and maintenance of the lateral access corridor.

In one exemplary embodiment, the depth of the femoral nerve relative to one or more components of the tissue retraction assembly may be obtained prior to retracting tissue away from the access corridor. Localization of the depth of the femoral nerve relative to one or more components of the tissue retraction assembly may be accomplished via either an electrode body 90 with multiple electrode contacts 96 (FIGS. 19-20), a retractor blade 12 with multiple electrode contacts 114 (FIG. 25), a posterior shim element 120 with multiple electrode contacts 126 (FIG. 26-29), or an electrode body 100 with a single electrode 106 movable along at least a portion of the length of the posterior blade 12 (FIG. 21-24). Monopolar or bipolar stimulation may be used to find the location (specific electrode or electrode position) that elicits the lowest stimulation threshold intensity. The stimulation threshold intensities may be acquired using either a linear or non-linear hunting algorithm, one example of which is set forth in the above-referenced '045 patent. The electrode location that elicits the lowest stimulation threshold intensity is the location that the femoral nerve is closest to, which is indicative of depth of the femoral nerve as well as the optimal position for recording a compound nerve action potential (CNAP), as will be described in detail below.

According to one exemplary embodiment, the femoral nerve may be stimulated with stimulation electrodes (preferably surface electrodes) placed over the inguinal ligament ipsilateral to the operative site. For example, if the lateral access corridor is performed on the patient's right side, the stimulation electrodes should be placed over the right inguinal ligament. Because the femoral nerve is a mixed nerve, meaning that it has motor nerve components and sensory nerve components, the corresponding neurophysiologic response is a CNAP. Depending on the location of the stimulation electrodes relative to the femoral nerve at the inguinal ligament, the stimulation current required to evoke a CNAP will vary depending on the resistance caused by the patient's bodily tissue. In other words, the closer the stimulation electrode to the femoral nerve, the less current will be required to cause the nerve to depolarize. By way of example only, anywhere from 10 to 50 mA of current may be required to elicit a CNAP.

The amount of current required to elicit a significant CNAP ($I_{Thresh}$) may then be calculated for the CNAP response. $I_{Thresh}$ provides a measure of the communication between the recording electrode (adjacent and/or associated with the retractor blade) and the nerve. According to one or more implementations, a threshold hunting algorithm is used to quickly find $I_{Thresh}$. In one such embodiment, the threshold hunting algorithm is used to quickly find $I_{Thresh}$ using a bracketing method and a bisection method. The bracketing method quickly finds a range (bracket) of stimulation currents that must contain $I_{Thresh}$ and the bisection method narrows the bracket until $I_{Thresh}$ is known within a specified accuracy. In another such implementation, the threshold hunting algorithm may begin by immediately determining an appropriate safety level and entering the bracketing phase by initiating stimulation at one or more boundary current levels. Once the safety level is known, the algorithm may transition to the bracketing and bisection phases to determine the actual $I_{Thresh}$ value. The algorithms described in brief detail above for finding $I_{Thresh}$ for a compound nerve are the same as that shown and described in more detail in the above-referenced '045 patent for finding $I_{Thresh}$ on a motor nerve.

Figure 34:
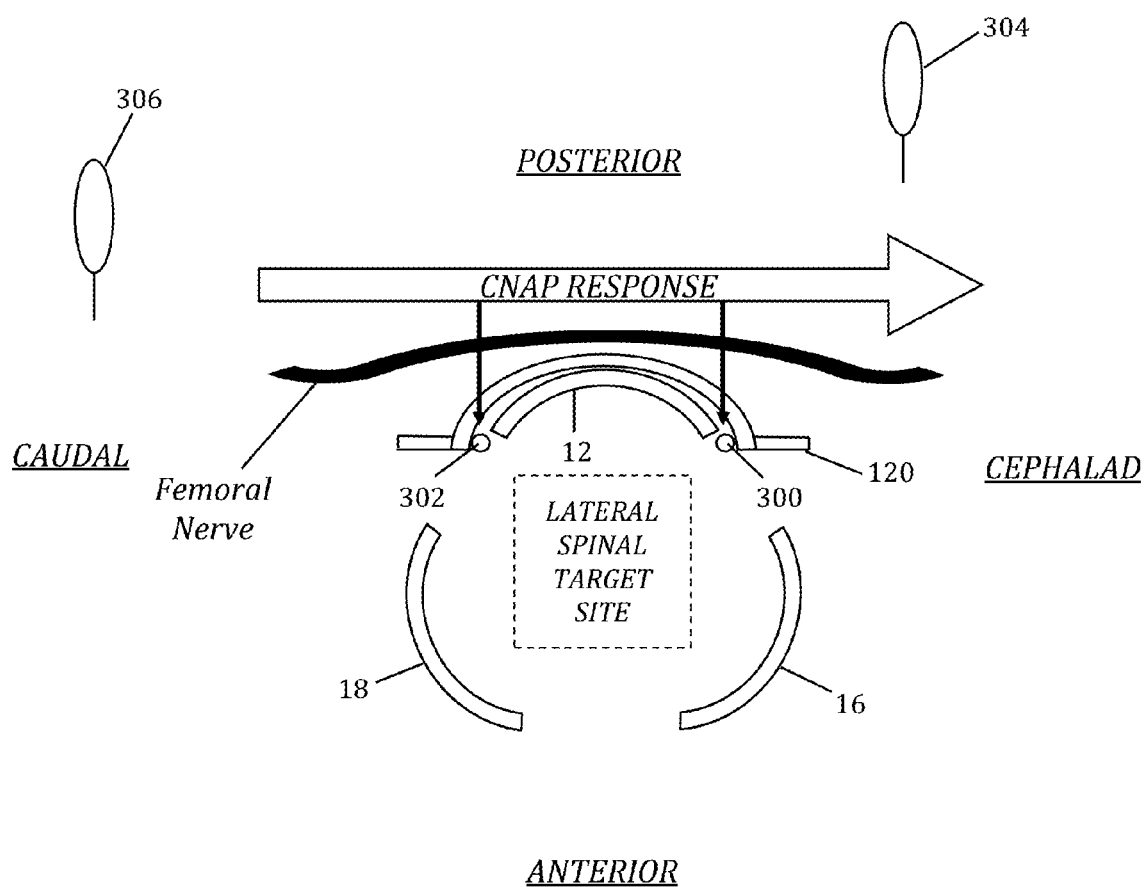
FIG. 34 illustrates an example of a first configuration for performing neurophysiologic monitoring of a nerve across a site of retraction to evaluate the health and status of the nerve for possible compression according to one embodiment.

One or more recording electrodes are placed at some location near the site of retraction and are configured to record the CNAP responses. According to some implementations, one recording electrode is placed superior to (and preferably adjacent to) the posterior blade. According to other implementations, for example the implementation diagrammed in FIG. 34, one recording electrode 300 is placed superior (i.e. cephalad) to the posterior blade 12 and one recording electrode 302 is placed inferior (i.e. caudal) to the posterior blade 12. As described above, one or more stimulation electrodes 306 are placed over the ipsilateral inguinal ligament, and then stimulation current is applied to the stimulation electrode(s) 306. A differential recording is then made based on the CNAP recordings at these two locations. As shown generally in the diagram in FIG. 34, the recording electrode/electrodes 300, 302 are preferably placed adjacent to the posterior blade 12. By way of example only, the recording electrodes 300, 302 (or sets of recording electrodes) may be disposed on the side of the retractor blade 12 (preferably) adjacent to the retractor blade 12 and connected to the retractor blade 12 via a track (not shown) on the side of the retractor blade 12, disposed on a shim 120 attached to the retractor blade 12 (FIGS. 26-29), or standalone (for example, a ball-tip probe) (not shown). According to some implementations, the location of the recording electrode 300, 302 may be adjustable based on the depth of the femoral nerve relative to the retractor blade 12. In any or all of these embodiments, the recording electrodes 300, 302 may be paired with one or more reference electrodes 304.

The neuromonitoring system may record CNAPs at multiple time points during the surgical procedure and compare them to one or more previous responses. By way of example only, one or more responses may be obtained prior to creation of the surgical corridor, prior to insertion of the retractor into the surgical corridor, after the retraction of tissue, and periodically while the retractor maintains the surgical corridor. Preferably, a baseline CNAP is obtained prior to retraction that can serve as a comparison for responses obtained later in the surgical procedure. Changes in CNAP response data may be indicative of a possible nerve deficit based on the time of and/or the extent of retraction. Measuring CNAP responses from the femoral nerve on either side of the retraction site can provide valuable information of the effect of retraction at the source. According to one example, the amount of current ($I_{Thresh}$) required to elicit a significant CNAP (percent or raw number) may be compared to the baseline. According to another example, the amplitude of the CNAP response (percent or raw number) may be compared to the baseline. According to another example, the latency of the CNAP response (percent or raw number) may be compared to the baseline. According to another example, the presence or absence of a CNAP response may be compared to the baseline. The neuromonitoring system may quickly and accurately determine this data and convey the useful information in a simple and easily comprehensible manner for interpretation by a surgeon, neurophysiologist, or other medical personnel. It is contemplated that the control unit of the neuromonitoring system may automatically ascertain this information and/or communicate any of numerical, graphic, audio, and visual feedback corresponding to one or more of these findings. Armed with this useful information, the surgeon may detect a problem or potential problem early and then act to avoid and/or mitigate the problem.

Figure 35:
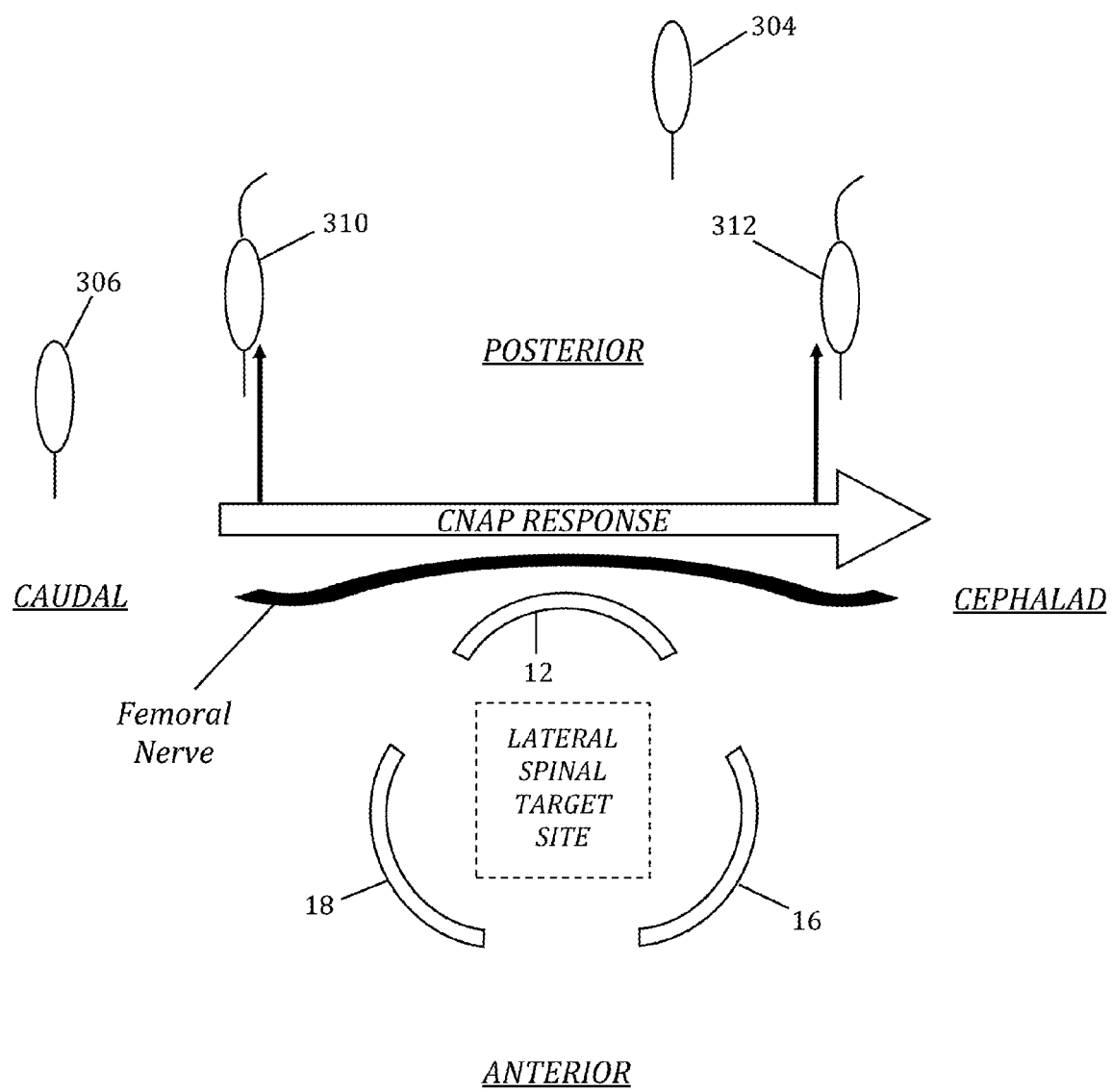
FIG. 35 illustrates an example of a second configuration for performing neurophysiologic monitoring of a nerve across a site of retraction to evaluate the health and status of the nerve for possible compression according to one embodiment.

According to another exemplary embodiment, the neuromonitoring system may perform nerve proximity testing on the femoral nerve utilizing stimulating electrodes placed caudal to the site of retraction as set forth above and recording electrodes (preferably insulated needle electrodes) placed in one or more interspinous ligaments. According to some implementations, for example the implementation diagrammed in FIG. 35, one recording electrode 310 is placed in the interspinous ligament of the operative level or the adjacent inferior level (off-midline and ipsilateral to the operative site) and another recording electrode 312 is placed in the adjacent superior interspinous ligament. As described above, one or more stimulation electrodes 306 are placed over the ipsilateral inguinal ligament, and then stimulation current is applied to the stimulation electrode(s) 306. Differential recordings are made based on the CNAP recordings acquired at both locations. According to other implementations, recording electrodes may be placed off-midline in the adjacent superior interspinous ligament ipsilateral and contralateral to the operative site. In accordance with the implementations of this exemplary embodiment, CNAPs may be recorded at multiple time points during the procedure and compared to previous responses, as set forth above. Additionally, in those implementations providing for recordings in the ipsilateral and contralateral interspinous ligaments, recordings from the recording electrodes ipsilateral to the operative site may be compared to the non-operative side to measure the effect that the retractor might be having on the ipsilateral femoral nerve over time. The neuromonitoring system may quickly and accurately determine this data and convey the useful information in a simple and easily comprehensible manner for interpretation by a surgeon, neurophysiologist, or other medical personnel. It is contemplated that the control unit of the neuromonitoring system may communicate any of numerical, graphic, audio, and visual feedback corresponding to one or more of these findings. Armed with this useful information, the surgeon may detect a problem or potential problem early and then act to avoid and/or mitigate the problem.

As evident from the above discussion and drawings, the present disclosure accomplishes the goal of gaining access a surgical target site in a fashion less invasive than traditional "open" surgeries and, moreover, does so in a manner that provides the ability to access such a surgical target site regardless of the neural structures required to be passed through (or near) in order to establish an operative corridor to the surgical target site. The present disclosure furthermore provides the ability to perform neural monitoring in the tissue or regions adjacent the surgical target site during any procedures performed after the operative corridor has been established.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the disclosure is to cover all modifications, equivalents, and alternatives falling within the spirit and scope of the disclosure as defined herein. For example, any of the features of a particular example described herein may be used with any other example described herein without departing from the scope of the present disclosure.

We claim:

1. A method for determining at least one of the depth, proximity, health, and status of the femoral nerve during lateral lumbar spine surgery, comprising:
    establishing a lateral, trans-psoas operative corridor to a surgical target site in the lumbar spine using a retractor assembly including a retractor body and a plurality of retractor blades extending generally perpendicularly to the retractor body, the retractor body being operable to separate the plurality of retractor blades relative to each to retract tissue away from the interior of the retractor blades when the tissue retractor is advanced to the surgical target site and the retractor blades are separated to thereby form an operative corridor to the surgical target site, wherein at least one of the plurality of retractor blades includes at least two electrode members associated with the at least one retractor blade, the at least two electrode contacts configured to at least one of transmit an electrical stimulation signal to tissue adjacent the distal portion of the at least one retractor blade and record an evoked neurophysiologic response received by the at least one retractor blade;
    placing at least one stimulation electrode in position to stimulate the inguinal ligament ipsilateral to the operative corridor;
    providing a stimulation current to the stimulation electrode;
    calculating a first $I_{Thresh}$ value at a first recording electrode positioned within the operative corridor adjacent to an inferior aspect of the at least one retractor blade;
    calculating a second $I_{Thresh}$ value at a second recording electrode positioned within the operative corridor adjacent to a superior aspect of the at least one retractor blade; and
    comparing the first and second $I_{Thresh}$ values to determine at least one of the depth, proximity, health, and status of the femoral nerve.

2. The method of claim 1, wherein, one of the at least one retractor blade is the posterior retractor blade.

3. The method of claim 2, wherein the at least two electrode contacts are integrally formed with the retractor blade.

4. The method of claim 3, wherein the at least two electrode contacts are integrally formed on opposite side surfaces of the retractor blade.

5. The method of claim 2, wherein the at least two electrode contacts are provide on a shim member removably attached to the retractor blade.

6. The method of claim 1, wherein the step of calculating a first $I_{Thresh}$ value comprises increasing the stimulation current at the stimulation electrode until a significant neuromuscular response is elicited at the first recording electrode.

7. The method of claim 1, wherein the step of calculating a second $I_{Thresh}$ value comprises increasing the stimulation current at the stimulation electrode until a significant neuromuscular response is elicited at the second recording electrode.

8. The method of claim 1, wherein the first and second $I_{Thresh}$ values are determined using one of a linear and a non-linear hunting algorithm.

9. The method of claim 1, wherein the steps of calculating the first $I_{Thresh}$ value, calculating the second $I_{Thresh}$ value, and comparing the first and second $I_{Thresh}$ values are performed more than once during the portions of the surgical procedure in which the tissue retractor assembly is maintaining the operative corridor.

* * * * *